US006667426B1

United States Patent
(12) United States Patent
Gonsalves et al.
(10) Patent No.: US 6,667,426 B1
(45) Date of Patent: Dec. 23, 2003

(54) GRAPEVINE FANLEAF VIRUS RESISTANCE IN GRAPEVINE EXPRESSING GRAPEVINE FANLEAF VIRUS COAT PROTEIN

(75) Inventors: Dennis Gonsalves, Hilo, HI (US); Baodi Xue, Nanjing (CN); Tania Krastanova, Prosser, WA (US); Kai-Shu Ling, Hollister, CA (US); Marc Fuchs, Colmar (FR)

(73) Assignee: Cornell Research Foundation, Inc., Ithaca, NY (US)

( * ) Notice: Subject to any disclaimer, the term of this patent is extended or adjusted under 35 U.S.C. 154(b) by 0 days.

(21) Appl. No.: 09/162,017

(22) Filed: Sep. 28, 1998

Related U.S. Application Data

(60) Provisional application No. 60/060,384, filed on Sep. 29, 1997.

(51) Int. Cl.[7] .......................... C12N 5/04; C12N 15/82; C12N 15/33; C12N 15/90; A01H 5/00

(52) U.S. Cl. .................... 800/280; 435/320.1; 435/419; 435/468; 536/23.72; 800/286; 800/301

(58) Field of Search ............................ 435/69.1, 320.1, 435/410, 419, 468; 536/24.5, 23.72; 800/278, 279, 280, 285, 286, 288, 295, 298, 301

(56) References Cited

U.S. PATENT DOCUMENTS

| | | | |
|---|---|---|---|
| 5,583,021 A | 12/1996 | Dougherty et al. | 435/468 |
| 5,596,132 A | 1/1997 | Zaitlin et al. | 800/279 |
| 5,633,449 A | 5/1997 | Zaitlin et al. | 800/279 |

OTHER PUBLICATIONS

Nejidat et al, Physiol. Plant., vol. 80, pp. 662–668, 1990.*
Smith et al, Plant Cell, vol. 6, pp. 1441–1453, 1994.*
Yepes et al, Phytopath., vol. 86, pp. 417–424, 1996.*
Nejidat et al., "Engineered resistance against plant virus diseases," *Physiologia Plantarum* 80:662–668 (1990).
Serghini et al., "In vitro Expression of a Chimeric Coat Protein Gene from Grapevine Fanleaf Virus (strain F 13)," *Archives of Virology* 117:297–304 (1991).
Fuchs et al., "Characterization and detection of grapevine fanleaf virus by using cDNA probes," *Phytopathology* 81:559–565 (1991).
Margis et al., "Cloning and in vitro characterization of the grapevine fanleaf virus proteinase cistron," *Virology* 185:779–787 (1991).
Pinck et al., "A satellite RNA in grapevine fanleaf virus strain F13," *J. Gen. Virol.*, 69:233–239 (1988).
Pinck et al., "Primary Structure and Location of the Genome–Linked Protein (VPg) of Grapevine Fanleaf Nepovirus," *FEBS Lett* 284:117–119 (1991).
Ritzenthaler et al., "Grapevine fanleaf nepovirus P38 putative movement protein is not transiently expressed and is a stable final maturation product in vivo," *J. Gen. Virol.* 76:907–915 (1995).
Serghini et al., "A rapid and efficient 'miniprep' for isolation of plasmid DNA," *Nucleic Acids Res.* 17:3604–3604 (1989).
Viry et al., "Biologically active transcripts from cloned cDNA of genomic Grapevine Fanleaf Nepovirus RNAs," *J. Gen. Virol.* 74:169–174 (1993).
Barbier et al., "Grapevine Genetically Transformed with the Coat Protein Gene of Grapevine Fanleaf Virus: An Analysis of Transformants," *12th Meeting of the International Council for the Study of Viruses and Virus–Like Diseases of the Grapevine, Extended Abstracts, Lisbon, Portugal*, p. 131 (1997).
Bardonnet et al., "Protection Against Virus Infection in Tobacco Plants Expressing the Coat Protein of Grapevine Fanleaf Nepovirus," *Plant Cell Reports* 13:357–360 (1994).
Brandt et al., "Coat Protein Gene Sequence of an Austrian Isolate of Grapevine Fanleaf Virus," *Archives of Virology* 140:157–164 (1995).
Fitch et al., "Virus Resistant Papaya Plants Derived from Tissues Bombarded with the Coat Protein Gene of Papaya Ringspot Virus," *BioTechnology* 10:1466–1472 (1992).
Fuchs et al., "The Nucleotide Sequence of Satellite RNA in Grapevine Fanleaf Virus, Strain F13," *Journal of General Virology* 70:955–962 (1989).
Kikkert et al., "Transgenic Plantlets of 'Chancellor' Grapevine (Vitis sp.) from Biolistic Transformation of Embryogenic Cell Suspensions," *Plant Cell Reports* 15:311–316 (1996).
Krastanova et al., "Transformation of Grapevine Rootstocks with the Coat Protein Gene of Grapevine Fanleaf Nepovirus," *Plant Cell Reports* 14:550–554 (1995).
Margis et al., "Genome Organization of Grapevine Fanleaf Nepovirus RNA2 Deduced from the 122K Polyprotein P2 in vitro Cleavage Products," *Journal of General Virology* 74:1919–1926 (1993).
Mauro et al., "High Efficiency Regeneration of Grapevine Plants Transformed with the GFLV Coat Protein Gene," *Plant Science* 112:97–106 (1995).
Ritzentbaler et al., "Complete Nucleotide Sequence and Genetic Organization of Grapevine Fanleaf Nepovirus RNA1," *Journal of General Virology* 72:2357–2365 (1991).

(List continued on next page.)

*Primary Examiner*—Ashwin Mehta
(74) *Attorney, Agent, or Firm*—Clark & Elbing LLP

(57) ABSTRACT

In general, the invention features a method for selecting a transgenic grapevine or grapevine component having increased resistance to a fanleaf disease, the method including the steps of: (a) transforming a grape plant cell with a grape nepovirus coat protein nucleic acid molecule or fragment thereof which is capable of being expressed in the plant cell; (b) regenerating a transgenic grapevine or grapevine component from the plant cell; and (c) selecting a transgenic grapevine or grapevine component which expresses, at a low level, the nucleic acid molecule or fragment thereof, wherein the low level expression increases the resistance of the transgenic grapevine or grapevine component to fanleaf disease. The invention also relates to an isolated nucleic acid molecule encoding a coat protein or fragment thereof of a 'Geneva' isolate of a grapevine nepovirus virus.

13 Claims, 5 Drawing Sheets

OTHER PUBLICATIONS

Figure 2:
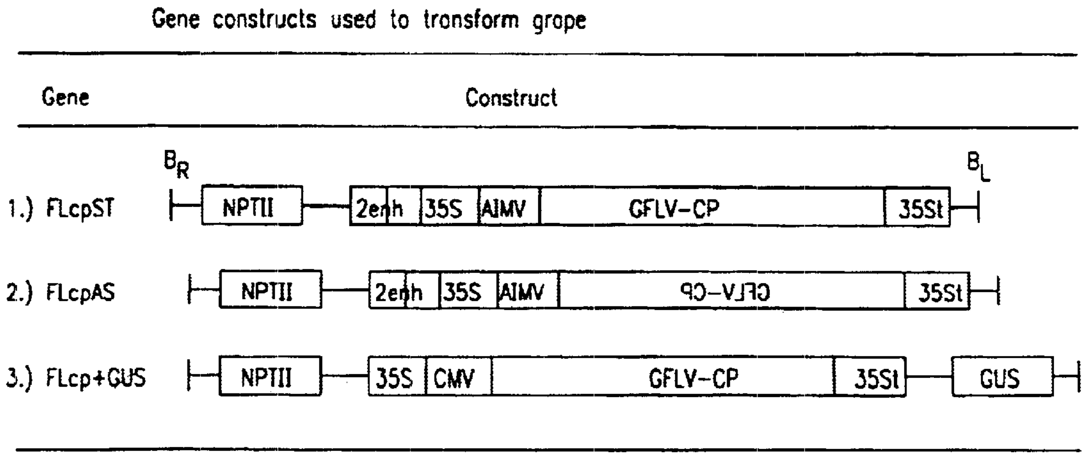

Sanchez et al., "cDNA Sequence of the Capsid Protein Gene and 3' Untranslated Region of a Fanleaf Isolate of Grapevine Fanleaf Virus," *Nucleic Acids Research* 19:5440 (1991).

Serghini et al., "RNA2 of Grapevine Fanleaf Virus: Sequence Analysis and Coat Protein Cistron Location," *Journal of General Virology* 71:1433–1441 (1990).

Tennant et al., "Differential Protection Against Papaya Ringspot Virus Isolates in Coat Protein Gene Transgenic Papaya and Classically Cross–Protected Papaya," *The Amer. Phytopath. Soc*. 84:1359–1366 (1994).

Xue et al., "Transformation of Grapevine Rootstocks Containing Genes from Grapevine Fanleaf Virus and Grapevine Leafroll Associated Closterovirus 2 and 3," *12$^{th}$ Meeting of the International Council for the Study of Viruses and Virus–Like Diseases of the Grapevine, Extended Abstracts, Lisbon, Portugal*, p. 137 (1997).

Grapevine fanleaf virus (GFLV) RNA1 for polyprotein, GenBank Accession No. D00915, Apr. 1994.

Grapevine fanleaf virus genomic RNA for capsid protein, GenBank Accession No. X60775, Oct. 1991.

Grapevine fanleaf virus, satellite RNA (RNA3), complete sequence, GenBank Accession No. D00442, Dec. 1992.

Grapevine fanleaf virus RNA2, deletion mutant, GenBank Accession No. U11770, Nov. 1995.

Grapevine fanleaf virus (GFLV–F13) RNA2 encoding capsid protein, GenBank Accession No. X16907, Sep. 1993.

RNA1=VPg, GenBank Accession No. S38553, Nov. 1992.

* cited by examiner

SEQ ID NO:1

```
    gtgagtggattagctggtagaggagtgatttatatccctaaggattgccaggcaaatagg
  1 ---------+---------+---------+---------+---------+---------+ 60
    cactcacctaatcgaccatctcctcactaaatatagggattcctaacggtccgtttatcc
          G  L  A  G  R  G  V  I  Y  I  P  K  D  C  Q  A  N  R
```

SEQ ID NO:2

```
    tacttgggcaccttaaatatacgagatatgatctcagattttaagggtgtccagtacgaa
 61 ---------+---------+---------+---------+---------+---------+ 120
    atgaacccgtggaatttatatgctctatactagagtctaaaattcccacaggtcatgctt
    Y  L  G  T  L  N  I  R  D  M  I  S  D  F  K  G  V  Q  Y  E

    aagtggataactgcaggattagtcatgcctacttttagaatagttgttaggctacctgca
121 ---------+---------+---------+---------+---------+---------+ 180
    ttcacctattgacgtcctaatcagtacggatgaaaatcttatcaacaatccgatggacgt
    K  W  I  T  A  G  L  V  M  P  T  F  R  I  V  V  R  L  P  A

    aatgcctttactggattgacgtgggtgatgagcttcgatgcttataaccggatagctagt
181 ---------+---------+---------+---------+---------+---------+ 240
    ttacggaaatgacctaactgcacccactactcgaagctacgaatattggcctatcgatca
    N  A  F  T  G  L  T  W  V  M  S  F  D  A  Y  N  R  I  A  S

    agaattactgctagtgcggatcctgtatacactctgtcagtcccacattggcttatccat
241 ---------+---------+---------+---------+---------+---------+ 300
    tcttaatgacgatcacgcctaggacatatgtgagacagtcagggtgtaaccgaataggta
    R  I  T  A  S  A  D  P  V  Y  T  L  S  V  P  H  W  L  I  H

    cataagttgggcacgtttacatgtgaaatagactatggagaattgtgtggtcacgccatg
301 ---------+---------+---------+---------+---------+---------+ 360
    gtattcaacccgtgcaaatgtacactttatctgatacctcttaacacaccagtgcggtac
    H  K  L  G  T  F  T  C  E  I  D  Y  G  E  L  C  G  H  A  M

    tggtttaagtccacaacctttgagtctccgaggctacacttcacgtgcttaacgggcaac
361 ---------+---------+---------+---------+---------+---------+ 420
    accaaattcaggtgttggaaactcagaggctccgatgtgaagtgcacgaattgcccgttg
    W  F  K  S  T  T  F  E  S  P  R  L  H  F  T  C  L  T  G  N

    aacaaagagttggcggcagactggcaagctgtcgtagaactgtatgcggaattggaagag
421 ---------+---------+---------+---------+---------+---------+ 480
    ttgtttctcaaccgccgtctgaccgttcgacagcatcttgacatacgccttaaccttctc
    N  K  E  L  A  A  D  W  Q  A  V  V  E  L  Y  A  E  L  E  E

    gccacgtccttccttgggaaaccaactttggtttttgacccaggtgcttttaatggtaaa
481 ---------+---------+---------+---------+---------+---------+ 540
    cggtgcaggaaggaaccctttggttgaaaccaaaaactgggtccacgaaaattaccattt
    A  T  S  F  L  G  K  P  T  L  V  F  D  P  G  A  F  N  G  K
```

FIG. 1A

```
     tttcaattcctgacttgccctcccatttctttgatctaacagccgttacggctcttagg
541  ---------+---------+---------+---------+---------+---------+ 600
     aaagttaaggactgaacgggagggtaaagaaactagattgtcggcaatgccgagaatcc
     F  Q  F  L  T  C  P  P  I  F  F  D  L  T  A  V  T  A  L  R

     agtactgggctaacgttaggacaagtcccaatggttggtactaccaaggtatacaatcta
601  ---------+---------+---------+---------+---------+---------+ 660
     tcatgacccgattgcaatcctgttcagggttaccaaccatgatggttccatatgttagat
     S  T  G  L  T  L  G  Q  V  P  M  V  G  T  T  K  V  Y  N  L

     aatagtactctcgtgagttgtattttaggaatgggaggtactattagaggaagggtgcac
661  ---------+---------+---------+---------+---------+---------+ 720
     ttatcatgagagcactcaacataaaatccttaccctccatgataatctccttcccacgtg
     N  S  T  L  V  S  C  I  L  G  M  G  G  T  I  R  G  R  V  H

     atttgtgcgccaatcttctatagtattgttttatgggttgttagtgagtggaacgggacc
721  ---------+---------+---------+---------+---------+---------+ 780
     taaacacgcggttagaagatatcataacaaaatacccaacaatcactcaccttgccctgg
     I  C  A  P  I  F  Y  S  I  V  L  W  V  V  S  E  W  N  G  T

     actatggattggaatgaacttttcaaatatcccggggtgtatgtagaagaggacggaagt
781  ---------+---------+---------+---------+---------+---------+ 840
     tgatacctaaccttacttgaaaagtttatagggccccacatacatcttctcctgccttca
     T  M  D  W  N  E  L  F  K  Y  P  G  V  Y  V  E  E  D  G  S

     tttgaagtcaaaatccgttctccatatcaccgaactcctgctagattgcttgctaaccaa
841  ---------+---------+---------+---------+---------+---------+ 900
     aaacttcagttttaggcaagaggtatagtggcttgaggacgatctaacgaacgattggtt
     F  E  V  K  I  R  S  P  Y  H  R  T  P  A  R  L  L  A  N  Q

     agccagagggatatgagctctctgaatttctatgcaatagcaggacctatagctccgtcg
901  ---------+---------+---------+---------+---------+---------+ 960
     tcggtctccctatactcgagagacttaaagatacgttatcgtcctggatatcgaggcagc
     S  Q  R  D  M  S  S  L  N  F  Y  A  I  A  G  P  I  A  P  S

     ggtgaaactgcacgacttcctatagtcgtgcagattgatgaaatcgtgcgcccagatctc
961  ---------+---------+---------+---------+---------+---------+ 1020
     ccactttgacgtgctgaaggatatcagcacgtctaactactttagcacgcgggtctagag
     G  E  T  A  R  L  P  I  V  V  Q  I  D  E  I  V  R  P  D  L

     tctctgccaagttttgaagatgattactttgtatgggtggacttttcagagttcactctt
1021 ---------+---------+---------+---------+---------+---------+ 1080
     agagacggttcaaaacttctactaatgaaacatacccacctgaaaagtctcaagtgagaa
     S  L  P  S  F  E  D  D  Y  F  V  W  V  D  F  S  E  F  T  L
```

FIG. 1B

```
     gacaaagaagaaatcgagattggttctcgcttctttgactttacttcaaatacttgtaga
1081 ---------+---------+---------+---------+---------+---------+ 1140
     ctgtttcttctttagctctaaccaagagcgaagaaactgaaatgaagtttatgaacatct
     D  K  E  E  I  E  I  G  S  R  F  F  D  F  T  S  N  T  C  R

     gtgtctatgggagaaaatccgtttgctgctatgattgcttgtcatggattgcacagtggc
1141 ---------+---------+---------+---------+---------+---------+ 1200
     cacagatacccctcttttaggcaaacgacgatactaacgaacagtacctaacgtgtcaccg
     V  S  M  G  E  N  P  F  A  A  M  I  A  C  H  G  L  H  S  H

     gtattggacctcaaatttcaatggagtctgaacaccgaatttggcaagagcagcgggagc
1201 ---------+---------+---------+---------+---------+---------+ 1260
     cataacctggagtttaaagttacctcagacttgtggcttaaaccgttctcgtcgccctcg
     V  L  D  L  K  F  Q  W  S  L  N  T  E  F  G  K  S  S  G  S

     attacaattacgaagctggtgggtgataaagccacaggcttggatgggccttcttgtgtt
1261 ---------+---------+---------+---------+---------+---------+ 1320
     taatgttaatgcttcgaccacccactatttcggtgtccgaacctacccggaagaacacaa
     I  T  I  T  K  L  V  G  D  K  A  T  G  L  D  G  P  S  C  V

     ttcgccatacaaaagctggagggaactgcagagttgttgattgggaattttgcaggagca
1321 ---------+---------+---------+---------+---------+---------+ 1380
     aagcggtatgttttcgacctcccttgacgtctcaacaactaacccttaaaacgtcctcgt
     F  A  I  Q  K  L  E  G  T  A  E  L  L  I  G  N  F  A  G  A

     aacccaaactctcatttctctctctacagtcggtggatggcgattaaactagatcaagca
1381 ---------+---------+---------+---------+---------+---------+ 1440
     ttgggtttgagagtaaagagagagatgtcagccacctaccgctaatttgatctagttcgt
     N  P  N  S  H  F  S  L  Y  S  R  W  M  A  I  K  L  D  Q  A

     aagagtatcaaagtactccgcgttttgtgtaaacctcgtccaggctttagtttttatgga
1441 ---------+---------+---------+---------+---------+---------+ 1500
     ttctcatagtttcatgaggcgcaaaacacatttggagcaggtccgaaatcaaaaatacct
     K  S  I  K  V  L  R  V  L  C  K  P  R  P  G  F  S  F  Y  G

     agaaccagcttcccagtctagggtatcttactttaaaagaccc
1501 ---------+---------+---------+---------+---1543
     tcttggtcgaagggtcagatcccatagaatgaaattttctggg
     R  T  S  F  P  V  *
```

FIG. 1C

Expression of the CP

| Transf. plantlets (%) | | | ELISA (A405, 1h) |
|---|---|---|---|
| 3309 | R. gloire | | |
| 61 | 53 | low | 0–0.200 |
| 26 | 22 | medium | 0.200–0.600 |
| 13 | 25 | high | > 0.600 |
| non-transf. control | | | 0.090 |
| buffer control | | | 0.020 |

SEQUENCE LISTING

```
<160> NUMBER OF SEQ ID NOS: 6

<210> SEQ ID NO 1
<211> LENGTH: 1542
<212> TYPE: DNA
<213> ORGANISM: Grapevine Fanleaf Virus Coat Protein Gene
<220> FEATURE:
<221> NAME/KEY: CDS
<222> LOCATION: (7)...(1518)

<400> SEQUENCE: 1
```

-continued

```
gtgagt gga tta gct ggt aga gga gtg att tat atc cct aag gat tgc        48
       Gly Leu Ala Gly Arg Gly Val Ile Tyr Ile Pro Lys Asp Cys
        1               5                  10

cag gca aat agg tac ttg ggc acc tta aat ata cga gat atg atc tca       96
Gln Ala Asn Arg Tyr Leu Gly Thr Leu Asn Ile Arg Asp Met Ile Ser
 15                  20                  25                  30

gat ttt aag ggt gtc cag tac gaa aag tgg ata act gca gga tta gtc      144
Asp Phe Lys Gly Val Gln Tyr Glu Lys Trp Ile Thr Ala Gly Leu Val
                 35                  40                  45

atg cct act ttt aga ata gtt gtt agg cta cct gca aat gcc ttt act      192
Met Pro Thr Phe Arg Ile Val Val Arg Leu Pro Ala Asn Ala Phe Thr
             50                  55                  60

gga ttg acg tgg gtg atg agc ttc gat gct tat aac cgg ata gct agt      240
Gly Leu Thr Trp Val Met Ser Phe Asp Ala Tyr Asn Arg Ile Ala Ser
         65                  70                  75

aga att act gct agt gcg gat cct gta tac act ctg tca gtc cca cat      288
Arg Ile Thr Ala Ser Ala Asp Pro Val Tyr Thr Leu Ser Val Pro His
     80                  85                  90

tgg ctt atc cat cat aag ttg ggc acg ttt aca tgt gaa ata gac tat      336
Trp Leu Ile His His Lys Leu Gly Thr Phe Thr Cys Glu Ile Asp Tyr
 95                 100                 105                 110

gga gaa ttg tgt ggt cac gcc atg tgg ttt aag tcc aca acc ttt gag      384
Gly Glu Leu Cys Gly His Ala Met Trp Phe Lys Ser Thr Thr Phe Glu
                115                 120                 125

tct ccg agg cta cac ttc acg tgc tta acg ggc aac aac aaa gag ttg      432
Ser Pro Arg Leu His Phe Thr Cys Leu Thr Gly Asn Asn Lys Glu Leu
            130                 135                 140

gcg gca gac tgg caa gct gtc gta gaa ctg tat gcg gaa ttg gaa gag      480
Ala Ala Asp Trp Gln Ala Val Val Glu Leu Tyr Ala Glu Leu Glu Glu
        145                 150                 155

gcc acg tcc ttc ctt ggg aaa cca act ttg gtt ttt gac cca ggt gct      528
Ala Thr Ser Phe Leu Gly Lys Pro Thr Leu Val Phe Asp Pro Gly Ala
    160                 165                 170

ttt aat ggt aaa ttt caa ttc ctg act tgc cct ccc att ttc ttt gat      576
Phe Asn Gly Lys Phe Gln Phe Leu Thr Cys Pro Pro Ile Phe Phe Asp
175                 180                 185                 190

cta aca gcc gtt acg gct ctt agg agt act ggg cta acg tta gga caa      624
Leu Thr Ala Val Thr Ala Leu Arg Ser Thr Gly Leu Thr Leu Gly Gln
                195                 200                 205

gtc cca atg gtt ggt act acc aag gta tac aat cta aat agt act ctc      672
Val Pro Met Val Gly Thr Thr Lys Val Tyr Asn Leu Asn Ser Thr Leu
            210                 215                 220

gtg agt tgt att tta gga atg gga ggt act att aga gga agg gtg cac      720
Val Ser Cys Ile Leu Gly Met Gly Gly Thr Ile Arg Gly Arg Val His
        225                 230                 235

att tgt gcg cca atc ttc tat agt att gtt tta tgg gtt gtt agt gag      768
Ile Cys Ala Pro Ile Phe Tyr Ser Ile Val Leu Trp Val Val Ser Glu
    240                 245                 250

tgg aac ggg acc act atg gat tgg aat gaa ctt ttc aaa tat ccc ggg      816
Trp Asn Gly Thr Thr Met Asp Trp Asn Glu Leu Phe Lys Tyr Pro Gly
255                 260                 265                 270

gtg tat gta gaa gag gac gga agt ttt gaa gtc aaa atc cgt tct cca      864
Val Tyr Val Glu Glu Asp Gly Ser Phe Glu Val Lys Ile Arg Ser Pro
                275                 280                 285

tat cac cga act cct gct aga ttg ctt gct aac caa agc cag agg gat      912
Tyr His Arg Thr Pro Ala Arg Leu Leu Ala Asn Gln Ser Gln Arg Asp
            290                 295                 300

atg agc tct ctg aat ttc tat gca ata gca gga cct ata gct ccg tcg      960
Met Ser Ser Leu Asn Phe Tyr Ala Ile Ala Gly Pro Ile Ala Pro Ser
```

-continued

```
        305                 310                 315

ggt gaa act gca cga ctt cct ata gtc gtg cag att gat gaa atc gtg     1008
Gly Glu Thr Ala Arg Leu Pro Ile Val Val Gln Ile Asp Glu Ile Val
    320                 325                 330

cgc cca gat ctc tct ctg cca agt ttt gaa gat gat tac ttt gta tgg     1056
Arg Pro Asp Leu Ser Leu Pro Ser Phe Glu Asp Asp Tyr Phe Val Trp
335                 340                 345                 350

gtg gac ttt tca gag ttc act ctt gac aaa gaa gaa atc gag att ggt     1104
Val Asp Phe Ser Glu Phe Thr Leu Asp Lys Glu Glu Ile Glu Ile Gly
                355                 360                 365

tct cgc ttc ttt gac ttt act tca aat act tgt aga gtg tct atg gga     1152
Ser Arg Phe Phe Asp Phe Thr Ser Asn Thr Cys Arg Val Ser Met Gly
            370                 375                 380

gaa aat ccg ttt gct gct atg att gct tgt cat gga ttg cac agt ggc     1200
Glu Asn Pro Phe Ala Ala Met Ile Ala Cys His Gly Leu His Ser Gly
        385                 390                 395

gta ttg gac ctc aaa ttt caa tgg agt ctg aac acc gaa ttt ggc aag     1248
Val Leu Asp Leu Lys Phe Gln Trp Ser Leu Asn Thr Glu Phe Gly Lys
    400                 405                 410

agc agc ggg agc att aca att acg aag ctg gtg ggt gat aaa gcc aca     1296
Ser Ser Gly Ser Ile Thr Ile Thr Lys Leu Val Gly Asp Lys Ala Thr
415                 420                 425                 430

ggc ttg gat ggg cct tct tgt gtt ttc gcc ata caa aag ctg gag gga     1344
Gly Leu Asp Gly Pro Ser Cys Val Phe Ala Ile Gln Lys Leu Glu Gly
                435                 440                 445

act gca gag ttg ttg att ggg aat ttt gca gga gca aac cca aac tct     1392
Thr Ala Glu Leu Leu Ile Gly Asn Phe Ala Gly Ala Asn Pro Asn Ser
            450                 455                 460

cat ttc tct ctc tac agt cgg tgg atg gcg att aaa cta gat caa gca     1440
His Phe Ser Leu Tyr Ser Arg Trp Met Ala Ile Lys Leu Asp Gln Ala
        465                 470                 475

aag agt atc aaa gta ctc cgc gtt ttg tgt aaa cct cgt cca ggc ttt     1488
Lys Ser Ile Lys Val Leu Arg Val Leu Cys Lys Pro Arg Pro Gly Phe
    480                 485                 490

agt ttt tat gga aga acc agc ttc cca gtc tagggtatct tactttaaaa       1538
Ser Phe Tyr Gly Arg Thr Ser Phe Pro Val
495                 500

gacc                                                                1542


<210> SEQ ID NO 2
<211> LENGTH: 504
<212> TYPE: PRT
<213> ORGANISM: Grapevine Fanleaf Virus Coat Protein

<400> SEQUENCE: 2

Gly Leu Ala Gly Arg Gly Val Ile Tyr Ile Pro Lys Asp Cys Gln Ala
 1               5                  10                  15

Asn Arg Tyr Leu Gly Thr Leu Asn Ile Arg Asp Met Ile Ser Asp Phe
            20                  25                  30

Lys Gly Val Gln Tyr Glu Lys Trp Ile Thr Ala Gly Leu Val Met Pro
        35                  40                  45

Thr Phe Arg Ile Val Val Arg Leu Pro Ala Asn Ala Phe Thr Gly Leu
    50                  55                  60

Thr Trp Val Met Ser Phe Asp Ala Tyr Asn Arg Ile Ala Ser Arg Ile
65                  70                  75                  80

Thr Ala Ser Ala Asp Pro Val Tyr Thr Leu Ser Val Pro His Trp Leu
                85                  90                  95

Ile His His Lys Leu Gly Thr Phe Thr Cys Glu Ile Asp Tyr Gly Glu
```

-continued

```
            100                 105                 110

Leu Cys Gly His Ala Met Trp Phe Lys Ser Thr Thr Phe Glu Ser Pro
        115                 120                 125

Arg Leu His Phe Thr Cys Leu Thr Gly Asn Asn Lys Glu Leu Ala Ala
    130                 135                 140

Asp Trp Gln Ala Val Val Glu Leu Tyr Ala Glu Leu Glu Glu Ala Thr
145                 150                 155                 160

Ser Phe Leu Gly Lys Pro Thr Leu Val Phe Asp Pro Gly Ala Phe Asn
                165                 170                 175

Gly Lys Phe Gln Phe Leu Thr Cys Pro Pro Ile Phe Phe Asp Leu Thr
            180                 185                 190

Ala Val Thr Ala Leu Arg Ser Thr Gly Leu Thr Leu Gly Gln Val Pro
        195                 200                 205

Met Val Gly Thr Thr Lys Val Tyr Asn Leu Asn Ser Thr Leu Val Ser
    210                 215                 220

Cys Ile Leu Gly Met Gly Gly Thr Ile Arg Gly Arg Val His Ile Cys
225                 230                 235                 240

Ala Pro Ile Phe Tyr Ser Ile Val Leu Trp Val Val Ser Glu Trp Asn
                245                 250                 255

Gly Thr Thr Met Asp Trp Asn Glu Leu Phe Lys Tyr Pro Gly Val Tyr
            260                 265                 270

Val Glu Glu Asp Gly Ser Phe Glu Val Lys Ile Arg Ser Pro Tyr His
        275                 280                 285

Arg Thr Pro Ala Arg Leu Leu Ala Asn Gln Ser Gln Arg Asp Met Ser
    290                 295                 300

Ser Leu Asn Phe Tyr Ala Ile Ala Gly Pro Ile Ala Pro Ser Gly Glu
305                 310                 315                 320

Thr Ala Arg Leu Pro Ile Val Val Gln Ile Asp Glu Ile Val Arg Pro
                325                 330                 335

Asp Leu Ser Leu Pro Ser Phe Glu Asp Asp Tyr Phe Val Trp Val Asp
            340                 345                 350

Phe Ser Glu Phe Thr Leu Asp Lys Glu Glu Ile Glu Ile Gly Ser Arg
        355                 360                 365

Phe Phe Asp Phe Thr Ser Asn Thr Cys Arg Val Ser Met Gly Glu Asn
    370                 375                 380

Pro Phe Ala Ala Met Ile Ala Cys His Gly Leu His Ser Gly Val Leu
385                 390                 395                 400

Asp Leu Lys Phe Gln Trp Ser Leu Asn Thr Glu Phe Gly Lys Ser Ser
                405                 410                 415

Gly Ser Ile Thr Ile Thr Lys Leu Val Gly Asp Lys Ala Thr Gly Leu
            420                 425                 430

Asp Gly Pro Ser Cys Val Phe Ala Ile Gln Lys Leu Glu Gly Thr Ala
        435                 440                 445

Glu Leu Leu Ile Gly Asn Phe Ala Gly Ala Asn Pro Asn Ser His Phe
    450                 455                 460

Ser Leu Tyr Ser Arg Trp Met Ala Ile Lys Leu Asp Gln Ala Lys Ser
465                 470                 475                 480

Ile Lys Val Leu Arg Val Leu Cys Lys Pro Arg Pro Gly Phe Ser Phe
                485                 490                 495

Tyr Gly Arg Thr Ser Phe Pro Val
            500
```

<210> SEQ ID NO 3

-continued

```
<211> LENGTH: 42
<212> TYPE: DNA
<213> ORGANISM: Artificial Sequence
<220> FEATURE:
<223> OTHER INFORMATION: Primer

<400> SEQUENCE: 3

cgtcagtcta gaccatggtg agaggattag ctggtagagg ag                42


<210> SEQ ID NO 4
<211> LENGTH: 30
<212> TYPE: DNA
<213> ORGANISM: Artificial Sequence
<220> FEATURE:
<223> OTHER INFORMATION: Primer

<400> SEQUENCE: 4

ctgtaccatg gtcttttaaa gtcagatacc                              30


<210> SEQ ID NO 5
<211> LENGTH: 33
<212> TYPE: DNA
<213> ORGANISM: Artificial Sequence
<220> FEATURE:
<223> OTHER INFORMATION: Primer

<400> SEQUENCE: 5

acgttaccat ggtgtagagg attagctggt aga                          33


<210> SEQ ID NO 6
<211> LENGTH: 32
<212> TYPE: DNA
<213> ORGANISM: Artificial Sequence
<220> FEATURE:
<223> OTHER INFORMATION: Primer

<400> SEQUENCE: 6

agtgctctcg agcaattgag acttttcaac aa                           32
```

GRAPEVINE FANLEAF VIRUS RESISTANCE IN GRAPEVINE EXPRESSING GRAPEVINE FANLEAF VIRUS COAT PROTEIN

CROSS REFERENCE TO RELATED APPLICATIONS

This application claims benefit from provisional application 60/060,384, filed on Sep. 29, 1997.

BACKGROUND OF THE INVENTION

This invention relates to disease resistance in plants.

Grapevine fanleaf virus (GFLV) is a grape nepovirus, which is transmitted from plant to plant by the dagger nematode, *Xiphinema index*. GFLV is the agent responsible for grapevine fanleaf disease, which occurs worldwide. The disease is named for the fan-leaf shaped appearance of GFLV-infected leaves. It is one of the most damaging and widespread diseases of grapevine. Symptoms of GFLV infection include abnormal shoot morphology and discolorations of the leaves, yielding a fan-like appearance (Agrios, *Plant Pathology*, $3^{rd}$ Edition, Academic Press, 1988, pp. 687–688). In addition, fruit production of infected vines is low, with grapevines producing small bunches having abnormal fruit set and ripening. Ultimately, infected grapevines degenerate and die.

Long range spread of GFLV is believed to be by use of infected planting material. While the natural host range is thought to be restricted to grape, GFLV is also transmissible to a wide range of herbaceous species by sap-rubbing inoculation. *Chenopodium quinoa* is a useful diagnostic species for the virus. In general, GFLV isolates are antigenically uniform and diagnosis by ELISA is a standard procedure.

Current strategies for controlling grapevine fanleaf disease and other nepovirus-induced diseases in vineyards include nematode control (for example, soil fumigation and use of other pesticides), breeding rootstocks for resistance to nematode feeding, breeding grapevines for resistance to GFLV, and planting certified disease-free grapevines.

SUMMARY OF THE INVENTION

In general, the invention features a method for producing and selecting a transgenic grapevine or grapevine component having increased resistance to a fanleaf disease. The method generally involves: (a) transforming a grape plant cell with a grape nepovirus coat protein nucleic acid molecule or fragment thereof (for example, a grape nepovirus coat protein nucleic acid molecule or fragment thereof having about 50% or greater sequence identity to SEQ ID NO: 1) which is capable of being expressed in a plant cell; (b) regenerating a transgenic grapevine or grapevine component from the plant cell; and (c) selecting a transgenic grapevine or grapevine component which expresses, at a low level, the nucleic acid molecule or fragment thereof, wherein the low level expression increases the resistance of the transgenic grapevine or grapevine component to fanleaf disease as compared to plants expressing the nucleic acid molecule at a high level. Low level expression of the grape nepovirus mRNA or of the expressed coat protein itself in the transgenic plant is measured according to standard methods including, without limitation, Northern blot analysis, ELISA, and inoculation of transgenic plants with virus and selection of resistant vines. In preferred embodiments, the nucleic acid molecule or fragment thereof is encoded by a transgene found in the transgenic grapevine.

In other preferred embodiments, the nucleic acid molecule or fragment thereof is expressed as in a sense or antisense orientation. In yet other preferred embodiments, such grape nepovirus coat protein nucleic acid molecules or fragments thereof (a non-limiting example being a sense nontranslatable grape nepovirus viral coat protein mRNA having an out-of-reading frame initiation ATG initiation codon with the remainder of the mRNA being out of frame) is expressed in the transgenic grapevine or grapevine component.

As is discussed above, the invention also includes fragments of a grape nepovirus coat protein nucleic acid molecule that facilitate, when expressed at low levels, an increased resistance of a transgenic grapevine or grapevine component thereof, to a fanleaf disease. Thus, grape nepovirus coat protein nucleic acid sequences described herein or portions thereof may be expressed in a plant to facilitate disease resistance. Sequences that mediate an increased resistance to a fanleaf disease are considered useful in the invention. As used herein, the term "fragment," as applied to sequences of a nucleic acid molecule, means at least 5 contiguous nucleotides, preferably at least 10 contiguous nucleotides, more preferably at least 20 to 30 contiguous nucleotides, and most preferably at least 40 to 80 or more contiguous nucleotides. Fragments of a grape nepovirus nucleic acid molecule can be produced and, subsequently, integrated into any standard expression vector (for example, those described herein) according to methods known to those skilled in the art.

Preferably, the grapevine useful in the invention is a member of the genus Vitis; and the grapevine component is a somatic embryo, a scion, a rootstock, or a mother block. In still other preferred embodiments, the fanleaf disease is grapevine fanleaf disease caused by a grape nepovirus. In yet other preferred embodiments, the grape nepovirus is a grapevine fanleaf virus or an arabis mosaic virus.

In another aspect, the invention features a vineyard including three or more transgenic grapevines or grapevine components each of which express, at a low level, a grape nepovirus coat protein nucleic acid molecule or fragment thereof, wherein the low level expression of the nucleic acid molecule or fragment thereof increases resistance of the transgenic grapevines or grapevine components in the vineyard to fanleaf disease.

In still another aspect, the invention features a substantially pure protein (for example, a recombinant protein) including an amino acid sequence having at least 97% amino acid identity to the amino acid sequence of the 'Geneva' isolate grape nepovirus coat protein shown in FIGS. 1A–1C (SEQ ID NO: 2). In preferred embodiments, the protein includes the amino acid sequence of the grape nepovirus coat protein shown in FIGS. 1A–1C (SEQ ID NO: 2). In yet other preferred embodiments, the protein has the amino acid sequence of the grape nepovirus coat protein shown in FIGS. 1A–1C (SEQ ID NO: 2) or fragments thereof.

In yet another aspect, the invention features an isolated nucleic acid molecule encoding a protein (for example, a recombinant protein) including an amino acid sequence having at least 97% amino acid identity to the amino acid sequence of the 'Geneva' isolate grape nepovirus coat protein shown in FIGS. 1A–1C (SEQ ID NO: 2). In preferred embodiments, the protein encoded by the nucleic acid molecule includes the amino acid sequence of SEQ ID NO: 2. In yet other preferred embodiments, the protein encoded by the nucleic acid molecule has the amino acid sequence of SEQ ID NO: 2 or a fragment thereof.

In another aspect, the invention features an isolated nucleic acid molecule (for example, a DNA molecule) that encodes a grape nepovirus coat protein that specifically hybridizes to a nucleic acid molecule that includes the nucleic acid sequence of FIGS. 1A–1C (SEQ ID NO: 1). Preferably, the specifically hybridizing nucleic acid molecule encodes a grape nepovirus sequence that mediates resistance when expressed at low levels in a grape plant cell to a fanleaf disease (for example, grapevine fanleaf disease). The invention also features an RNA transcript having a sequence complementary to any of the isolated nucleic acid molecules described above.

In related aspects, the invention further features a cell (for example, a prokaryotic cell or a eukaryotic cell such a mammalian cell or yeast cell) which includes an isolated nucleic acid molecule of the invention. In preferred embodiments, the cell is a bacterium (for example, *E. coli* or *Agrobacterium tumefaciens*) or is a plant cell (for example, a grape plant cell from any of the cultivars listed herein). Such a plant cell has resistance against a fanleaf disease (for example, grapevine fanleaf disease).

In still other related aspects, the invention further features a vector (for example, a plant expression vector) which includes an isolated nucleic acid molecule of the invention. In a preferred embodiment, the isolated nucleic acid molecule is operably linked to an expression control region that mediates expression of a protein encoded by the nucleic acid molecule (for example, a nucleic acid molecule (such as DNA) expressed as a sense translatable or a sense nontranslatable mRNA transcript, or as an antisense mRNA transcript).

In still other aspects, the invention features a transgenic plant or plant component (for example, a grapevine or grapevine component) that includes a nucleic acid molecule encoding a protein (for example, a recombinant protein) encoding an amino acid sequence having at least 97% amino acid identity to the amino acid sequence of the 'Geneva' isolate grape nepovirus coat protein shown in FIGS. 1A–1C (SEQ ID NO: 2). In preferred embodiments, such a transgenic plant or plant component includes a nucleic acid molecule of SEQ ID NO: 1. Moreover, fragments of these sequences may be made such that the nucleic acid molecule expresses a sense translatable, sense nontranslatable, or antisense RNA transcript. In still other preferred embodiments, the plant or plant component has the nucleotide sequence of SEQ ID NO: 1 or fragments thereof. Such plants or plant components which include the nucleic acid molecules of the invention have an increased level of resistance against a fanleaf disease caused by a grape nepovirus (for example, GFLV).

The methods and GFLV sequences described herein are useful for providing disease resistance or tolerance or both on a variety of grapevines (for example, Vitis spp., Vitis spp. hybrids, and all members of the subgenera Euvitis and Muscadinia), including scion or rootstock cultivars. Exemplary scion cultivars include, without limitation, those which are referred to as table or raisin grapes and those used in wine production such as Cabernet Franc, Cabernet Sauvignon, Chardonnay (for example, CH 01, CH 02, CH Dijon), Merlot, Pinot Noir (PN, PN Dijon), Semillon, White Riesling, Lambrusco, Thompson Seedless, Autumn Seedless, Niagrara Seedless, and Seval Blanc. Rootstock cultivars that are useful in the invention include, without limitation, *Vitis rupestris* Constantia, *Vitis rupestris* St. George, *Vitis california, Vitis girdiana, Vitis rotundifolia, Vitis rotundifolia* Carlos, Richter 110 (*Vitis berlandieri x rupestris*), 101–14 Millarder et de Grasset (*Vitis riparia x rupestris*), Teleki 5C (*Vitis berlandieri x riparia*), 3309 Courderc (*Vitis riparia x rupestris*), Riparia Gloire de Montpellier (*Vitis riparia*), 5BB Teleki (selection Kober, *Vitis berlandieri x riparia*), $SO_4$ (*Vitis berlandieri x rupestris*), 41B Millardet (*Vitis vinifera x berlandieri*), and 039-16 (*Vitis vinifera x Muscadinia*).

The invention also features scions, rootstocks, somatic or zygotic embryos, cells, or seeds that are produced from any of the transgenic grapevines or grapevine components described herein.

By "nontranslatable" is meant an m-RNA sequence that is not translated into a protein. Examples of such nontranslatable sequences include, without limitation, sequences including an initiation ATG codon followed by an engineered frameshift mutation and stop codon to prevent translation of the mRNA into a protein. Grape nepovirus coat protein genes expressing such nontranslatable mRNA sequences may be constructed according to standard methods (for example, those described herein).

By "low level expression" is meant a level of grape nepovirus coat protein gene expression in a transgenic plant that is greater than zero and that is sufficiently low to impart fanleaf disease resistance. "High level expression" refers to-the level of gene expression found in a transgenic plant expressing a coat protein gene that is too high to confer resistance to the disease. Exemplary methods for analyzing low level expression of a grape nepovirus coat protein gene includes, without limitation, Northern blot analysis for detection of a mRNA transcript, as well as immunological techniques such as ELISA for detection of a protein.

By "substantially identical" is meant a protein or nucleic acid molecule exhibiting at least 97%, and preferably 98%, or most preferably 99% identity to a reference amino acid sequence (for example, the amino acid sequence shown in FIGS. 1A–1C; SEQ ID NO: 2) or nucleic acid sequence (for example, the nucleic acid sequences shown in FIGS. 1A–1C; SEQ ID NO: 1). For proteins, the length of comparison sequences will generally be at least 16 amino acids, preferably at least 20 amino acids, more preferably at least 25 amino acids, and most preferably 35 amino acids or greater. For nucleic acids, the length of comparison sequences will generally be at least 50 nucleotides, preferably at least 60 nucleotides, more preferably at least 75 nucleotides, and most preferably 110 nucleotides or greater.

Sequence identity, at the amino acid or nucleic acid levels, is typically measured using sequence analysis software (for example, Sequence Analysis Software Package of the Genetics Computer Group, University of Wisconsin Biotechnology Center, 1710 University Avenue, Madison, Wis. 53705, BLAST, or PILEUP/PRETTYBOX programs). Such software matches identical or similar sequences by assigning degrees of homology to various substitutions, deletions, and/or other modifications. Conservative amino acid substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine.

By a "substantially pure protein" is meant a grape nepovirus coat protein (for example, the coat protein from the Geneva, N.Y. grape nepovirus isolate (FIGS. 1A–1C; SEQ ID NO: 2)) that has been separated from components which naturally accompany it. Typically, the protein is substantially pure when it is at least 60%, by weight, free from the proteins and naturally-occurring organic molecules with which it is naturally associated. Preferably, the preparation is at least 75%, more preferably at least 90%, and most preferably at least 99%, by weight, protein. A substantially pure protein (for example, the coat protein of the 'Geneva' grape nepovirus isolate) may be obtained, for example, by extraction from a natural source (for example, a GFLV-CP infected plant such as *C. quinoa*); by expression of a recombinant nucleic acid encoding a protein; or by chemically synthesizing the protein. Purity can be measured by any appropriate method, for example, column chromatography, polyacrylamide gel electrophoresis, or by HPLC analysis.

By "isolated nucleic acid molecule" is meant a nucleic acid molecule (for example, DNA) that is free of the nucleic acids which, in the naturally-occurring genome of the organism from which the nucleic acid molecule of the invention is derived, flank the nucleic acid molecule. The term therefore includes, for example, a recombinant DNA that is incorporated into a vector; into an autonomously replicating plasmid or virus; or into the genomic DNA of a prokaryote or eukaryote; or that exists as a separate molecule (for example, a cDNA or a genomic or cDNA fragment produced by PCR or restriction endonuclease digestion) independent of other sequences. It also includes a recombinant DNA which is part of a hybrid gene encoding additional protein sequence.

By "specifically hybridizes" is meant that a nucleic acid molecule that is capable of hybridizing to a nucleic acid sequence (for example, DNA) at least under low stringency conditions, and preferably under high stringency conditions.

By "protein" is meant any chain of amino acids, including polypeptides, regardless of length or post-translational modification (for example, glycosylation or phosphorylation), including polypeptides.

By "positioned for expression" is meant that the nucleic acid molecule (for example, DNA) is positioned adjacent to a sequence which directs transcription of the nucleic acid molecule (for example, a gene expressing a nontranslatable antisense sequence or sense nontranslatable sequence).

By "expression control region" is meant any minimal sequence sufficient to direct transcription. Included in the invention are promoter and enhancer elements that are sufficient to render promoter-dependent gene expression controllable for cell-, tissue-, or organ-specific gene expression, or elements that are inducible by external signals or agents (for example, light-, pathogen-, wound-, stress- or hormone-inducible elements; or constitutive elements); such elements may be located in the 5' or 3' regions of the native gene or engineered into a transgene construct.

By "operably linked" is meant that a gene and a regulatory sequence(s) are connected in such a way to permit gene expression when the appropriate molecules (for example, transcriptional activator proteins) are bound to the regulatory sequence(s).

By "plant cell" is meant any self-propagating cell bounded by a semi-permeable membrane and containing a plastid. A plant cell, as used herein, is obtained from, without limitation, seeds, suspension cultures, embryos, meristematic regions, callus tissue, protoplasts, leaves, roots, shoots, somatic and zygotic embryos, as well as any part of a reproductive or vegetative tissue or organ.

By "plant component" is meant a part, segment, or organ obtained from an intact plant or plant cell. Exemplary plant components include, without limitation, somatic embryos, leaves, fruits, scions and rootstocks.

By "vineyard" is meant a plot of land which includes three or more transgenic grapevines or grapevine components which were selected for low level expression of a grape nepovirus coat protein nucleic acid molecule or fragment thereof.

By "transgenic" is meant any cell which includes a nucleic acid molecule (for example, a DNA sequence) which is inserted by artifice into a cell and becomes part of the genome of the organism (in either an integrated or extrachromosomal fashion for example, a viral expression construct which includes a subgenomic promoter) which develops from that cell. As used herein, the transgenic organisms are generally transgenic grapevines or grapevine components and the nucleic acid molecule (for example, a transgene) is inserted by artifice into the nuclear or plastidic compartments of the plant cell. Preferably, such transgenic grapevine or grapevine component express at least one sense translatable, sense nontranslatable, or antisense grape nepovirus transcript (for example, a GFLV-CP antisense sequence).

By "transgene" is meant any piece of a nucleic acid molecule (for example, DNA) which is inserted by artifice into a cell, and becomes part of the organism (integrated into the genome or maintained extrachromosomally) which develops from that cell. Such a transgene may include a gene which is partly or entirely heterologous (i.e., foreign) to the transgenic organism, or may represent a gene homologous to an endogenous gene of the organism.

By "antisense nucleic acid sequence" is meant a nucleotide sequence that is complementary to a transcribed RNA. In general, such an antisense sequence will-usually be at least 15 nucleotides, preferably about 15–200 nucleotides, and more preferably 200–2,000 nucleotides in length. The antisense sequence may be complementary to all or a portion of the transcribed RNA nucleotide sequence (for example, a grape nepovirus sequence such as the GFLV-CP antisense constructs described herein or any of the GFLV sequences described in Brandt et al., *Arch. Virol.* 140: 157–164, 1995; Margis et al., *J. Gen. Virol.* 74: 1919–1926, 1993; Fuchs et al., *J. Gen Virol.* 955–962, 1989; Serghini et al., *J. Gen. Virol.* 71: 1433–1441, 1990; Bardonnet et al., *Plant Cell Reports* 13: 357–360, 1994; Krastanova et al., *Plant Cell Rep.* 14:550–554, 1995; Ritzenthaler et al., *J. Gen. Virol.* 72: 2357–2365, 1991; Mauro et al., *Plant Science*: 112: 97–106, 1995; and Sanchez et al., *Nucleic Acids. Res.* 19: 5440, 1992), and, as appreciated by those skilled in the art, the particular site or sites to which the antisense sequence binds as well as the length of the antisense sequence will vary, depending upon the degree of inhibition desired and the uniqueness of the antisense sequence. Preferably, a transcriptional construct expressing a grape nepovirus sequence (for example, a GFLV-CP antisense nucleotide sequence) includes, in the direction of transcription, an expression control region, the sequence coding for the antisense RNA on the sense strand, and a transcriptional termination region. Antisense grape nepovirus sequences (for example, GFLV sequences) may be constructed and expressed as described herein or as described, for example, in van der Krol et al., *Gene* 72: 45, 1988; Rodermel et al., *Cell* 55: 673, 1988; Mol et al., *FEBS Lett.* 268: 427, 1990; Weigel and Nilsson, *Nature* 377: 495, 1995; Cheung et al., *Cell* 82: 383, 1995); and U.S. Pat. No. 5,107,065.

By "increased resistance to a fanleaf disease" is meant a greater level of resistance to a fanleaf disease (for example, any disease caused by a grape nepovirus such as those caused by GFLV, arabis mosaic virus, and the like) in a transgenic grapevine (or grapevine component or cell or seed thereof) than the level of resistance relative to a control grapevine (for example, a non-transgenic grapevine). In preferred embodiments, the level of resistance in a transgenic grapevine is at least 5 to 10% (and preferably 20%, 30%, or 40%) greater than the resistance of a control grapevine. In other preferred embodiments, the level of resistance to fanleaf disease is 50% greater, 60% greater, and more preferably even 75% or 90% greater than a control grapevine; with up to 100% resistance as compared to a control grapevine being most preferred. The level of resistance is measured using conventional methods. For example, the level of resistance to fanleaf disease may be determined by comparing physical features and characteristics (for example, plant height and weight, or by comparing disease symptoms, for example, delayed lesion development, reduced lesion size, leaf wilting and curling, mottling and necrosis of leaves, deformity of canes, number of intemodes, mosiac rings on leaves, and discoloration of cells) of transgenic grapevines. Infectivity of a grape nepovirus (for example, a GFLV or an arabis mosaic virus) can also be monitored using, for example, standard ELISA.

As is discussed above, it has been discovered that the low level expression of a grape nepovirus sense-translatable coat protein gene, as well as an antisense sequence, provides transgenic grapevines with resistance against disease caused by a grape nepovirus. Accordingly, the invention provides a number of important advances and advantages for viticulturists. For example, by selecting transgenic grapevines which express low levels of a recombinant grape nepovirus coat protein gene and thus have increased resistance against grape nepovirus infection, the invention facilitates an effective and economical means for protection against grapevine fanleaf disease and other grape nepovirus-induced diseases. Such protection reduces or minimizes the need for traditional chemical practices (for example, soil fumigation) typically used by viticulturists for controlling the spread of a grape nepovirus and provides protection against these disease-causing pathogens. In addition, because grape plants expressing such grape nepovirus sequences are less vulnerable to grape nepovirus infection and fanleaf disease, the invention further provides for increased production efficiency, as well as for improvements in quality, color, flavor, and yield of grapes. Furthermore, because the invention reduces the necessity for chemical protection against grapevine pathogens, the invention also benefits the environment where the vineyards are planted. The invention may also be used in combination with cultivated rootstocks having resistance to soil-borne nematodes.

Other features and advantages of the invention will be apparent from the following description of the preferred embodiments thereof, and from the claims.

DETAILED DESCRIPTION

The drawings will first be described.

Drawings

FIGS. 1A, 1B, and 1C are schematic illustrations showing the nucleotide (SEQ ID NO: 1) and deduced amino acid sequence (SEQ ID NO: 2) of the coat protein of a Geneva, N.Y. grape nepovirus isolate.

FIG. 2 is a schematic illustration showing the maps of the plant expression vectors containing different viral gene constructs. The gene constructs used to transform grape plants were as follows: (1) FlcpST: GFLV sense translatable coat protein gene in pGA482G; (2) FlcpAS: GFLV antisense coat protein gene in pGA482G; and (3) Flcp+GUS: GFLV sense translatable coat protein gene in pGA482GG. NPTII: Neomycin phosphotransferase II gene; 2enh: double cauliflower mosaic virus (CaMV) 35S enhancers; 35S: promoter CaMV 35S promoter; AIMV: alfalfa mosaic virus 5' untranslatable leader sequence; CMV: cucumber mosaic virus-C 5' untranslated leader sequence; 35St: CaMV 35S terminator; NOS: Nopaline synthase terminator;GUS: uidA gene; and $B_R$ and $B_L$: right border and left border sequences of the T-DNA, respectively.

Figure 3:
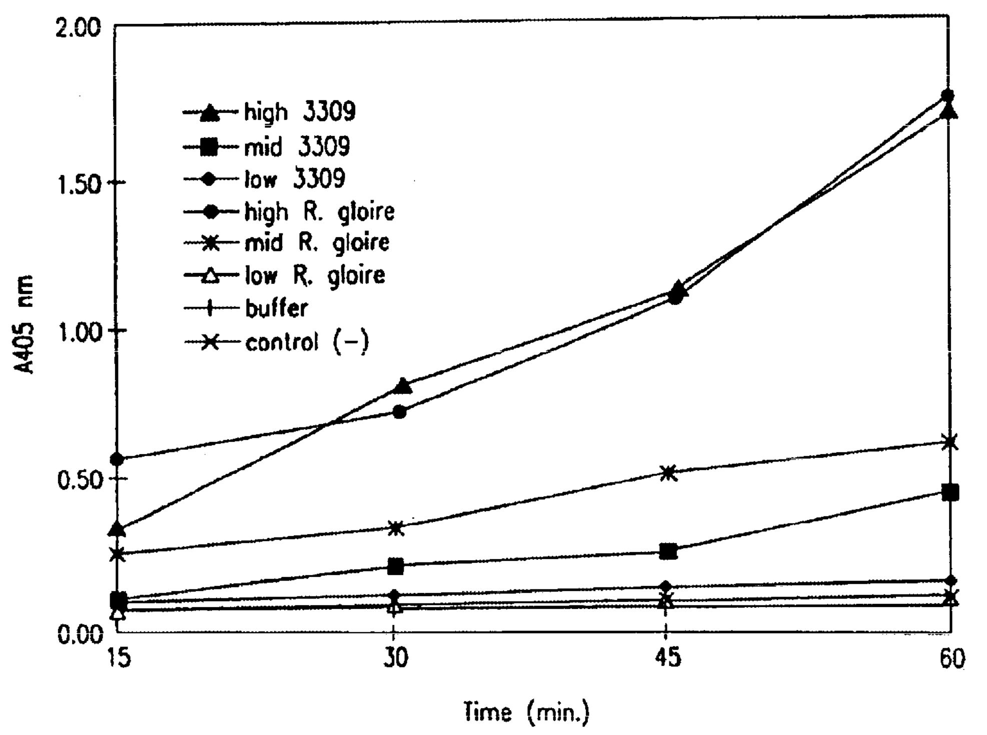

FIG. 3 shows the results of experiments analyzing the expression levels of grapevine fanleaf coat protein in transgenic 3309C and Gloire.

A description for the production of disease resistant transgenic grapevines now follows. Transgenic grape plants expressing either sense translatable, sense nontranslatable, or antisense sequences of grapevine fanleaf virus coat protein (GFLV-CP) genes were regenerated from embryogenic callus cultures derived from anthers of rootstocks (3309 Couderc ("3309C"), Riparia Gloire ("Gloire"), Teleki 5C ("5C"), 110 Richter ("110R"), SO4, and MGT 101-14 ("101-14")). Unexpectedly, transgenic plants expressing low levels of a recombinant grapevine fanleaf coat protein gene were found to be resistant to fanleaf disease.

The examples provided below are for the purpose of illustrating the invention, and should not be construed as limiting.

Results

Initiation of Embryogenic Callus and Embryogenesis

Callus was initiated from grape cultivars: Gloire, 3309C, 5C, 110R, and 101-14 on MSE medium (infra). Anthers from flower buds of the five rootstocks began to swell after one week in culture. After four weeks, a smooth, gelatinous, bright yellow callus developed. At this time, some embryos of Gloire, 3309C, and 110R were visible on the callus tissue. After eight weeks, all the calli were transferred to HMG medium (infra) to permit further development of the embryos. By the eighth week on HMG medium, many embryo clusters were induced from the callus tissue.

Plant Regeneration

After cultivation for eight to sixteen weeks in HMG medium, embryo clusters, and hypocotyls were found to develop from the calli. At the same time, secondary embryos were continually produced from the primary embryos. Embryo clusters were next transferred to MGC medium (infra) to increase embryo size and growth rate. However, fewer embryos were produced on MGC medium as compared to HMG medium for all rootstock cultivars that were examined. Embryo development of cultivar 110R was found to be dependent on the use of both media; HMG medium was required to induce many small secondary embryos and MGC medium was needed to simulate hypocotyl growth.

Hypocotyls were subsequently transferred onto a woody plant medium (Lloyd and McCown, infra) and shoots appeared within one to two months. The plantlets were generally induced at thirty to sixty-six frequency on woody plant medium.

The resulting plantlets were then transplanted to soil and kept in the greenhouse. Plants of Gloire, 5C, 110R, 101-14, and 3309C exhibited normal morphology.

Maintenance of Somatic Embryogenesis

A continuous supply of embryogenic calli were produced using an embryo cycling method; pieces of hypocotyl induced embryogenic callus on the MSE medium in two to three months. These calli were amenable for transformation because they developed many uniform embryos. Embryos of 5C required culture on MSE medium for three months, followed by culture on HMG medium for two to three months to induce the formation of embryos. The duration of time required for embryo cycling (embryogenic callus to hypocotyl and back to embryogenic callus) varied for the different cultivars; Riparia Gloire required two to three months, 3309C and 101-14 required five to six months, and 5C required six to seven months.

Transformation

Using standard techniques of molecular biology, a nucleotide sequence encoding a coat protein gene of a Geneva, N.Y. grape nepovirus isolate was isolated and characterized. The nucleic acid sequence (SEQ ID NO: 1) and deduced amino acid sequence (SEQ ID NO: 2) of the 'Geneva' isolate coat protein gene are shown in FIGS. 1A–1C. These sequences were also compared to three different GFLV isolates from France (Serghini et al., *J. Gen. Virol.* 71: 1433–1442, 1990), California (Sanchez et al., *Nucleic Acids Res.* 19 5440, 1991), and Austria (Brandt et al., *Arch. Virol.* 140: 157–164, 1995) using the Prettybox program. The percentage of identity of the amino acid sequences of the French, Californian, and Austrian isolates with the 'Geneva' isolate was 96.4%, 95.0%, and 95.4%, respectively.

Three different gene constructs (sense translatable, sense nontranslatable, and antisense) were used to transform grape (FIG. 2). Small somatic embryos and embryogenic calli of the five rootstocks Gloire, 3309C, 110R, 5C, and 101-14 were cocultivated with *A. tumefaciens* strain C58Z707 harboring binary vectors carrying the coat protein gene of the 'Geneva' isolate. After cocultivation, somatic embryos were transferred to HMG or MSE media with cefotaxime, carbenicillin, and kanamycin to select transgenic embryos and plants. Transgenic plants were thus generated.

Analysis of Transgenic Plants

In an experiment with a GFLV-CP sense-translatable and β-glucuronidase gene expression constructs (FLcpST+GUS, FIG. 2), putative transgenic plants of Gloire and of 110R were assayed for GUS activity, the NPTII gene, and expression of the GFLV-CP gene by ELISA. By PCR analysis, about 93% of the transformed Gloire plants were found to have the GFLV-CP gene of the expected size, yet these plants were negative for GFLV expression by ELISA.

These results indicated that GFLV-CP gene expression in the Gloire transgenics was too low to detect using ELISA. In contrast cultivar 3309C was transformed with GFLV-CP sense-translatable construct in a vector without GUS. We analyzed coat protein expression of putative transgenic plants, and found that 97.7% ELISA positive plants. Among these plants, 37.7% showed low expression ($0.1<OD_{405}>0.5$), 30.7% showed medium expression ($0.5<OD_{405}>1.0$), and 31.0% had high expression ($OD_{405}>1.0$). Nontransformed control plants were negative ($OD_{405}<0.020$).

In an another series of experiments, ELISA results also revealed different levels of expression of GFLV coat protein gene in transgenic plants of 3309C and Gloire. Low coat protein gene expression was observed in 61% and 53% of the transformed 3309C and Gloire, respectively. Medium coat protein gene expression was found in 26% and 22%, respectively. High coat protein gene expression was found in 13% and 25%, respectively, of the transformed 3309C and Gloire (FIG. 3).

Protection Against GFLV Infection

Transgenic plants were tested for GFLV resistance as follows. Plants were inocluated with GFLV by heterografting to GFLV-infected *C. quinoa* or by grafting to nontransgenic GFLV-infected cultivars according to standard methods. The plants were maintained for several months after inoculation and then were evaluated for disease resistance. Disease resistance was assessed by standard ELISA. The results of these experiments are shown in Tables I–V (below). In particular, as is shown in Table III, one transgenic line expressing the antisense expression constructs GFLVcpAntiS (FIG. 2) was found to resist GFLV infection.

TABLE I

ELISA Evaluation of Transgenic 110 Richter Heterografted with Infected *C. quinoa*

| Transgenic lines[1] | ELISA Apr. 31, 1997 | ELISA May 27, 1997 | ELISA Aug. 6, 1997 | ELISA Feb. 12, 1997 | (%) infected |
|---|---|---|---|---|---|
| #2 | 0/2 | 1/2 | 1/4 | 1/4 | 25.0 |
| #3 | 0/6 | 1/6 | 4/10 | 4/10 | 40.0 |
| #6 | 0/2 | nt | 1/2 | 1/2 | 50.0 |
| #8 | 0/2 | 2/2 | 2/5 | NT | 40.0 |
| #21 | 0/8 | nt | 8/8 | 8/8 | 100.0 |
| #41 | nt | 2/8 | 5/8 | NT | 62.0 |
| #45 | — | — | 2/2 | NT | 100.0 |
| #50 | — | 3/4 | 4/4 | 4/4 | 100.0 |
| #84 | — | 4/6 | 5/6 | 5/6 | 83.0 |
| Control | — | 6/8 | 14/16 | 14/16 | 88.0 |

[1]FLcpST + GUS (FIG. 2); NT: Not tested

TABLE II

ELISA Evaluation of Transgenic Riparia Gloire Heterografted with GFLV Infected *C. quinoa*

| Transgenic lines[1] | 2 months | 4–5 months | Total | (%) infected |
|---|---|---|---|---|
| #5 | 0/3 | 0/10 | 0/10 | 0 |
| #6 | 0/3 | 0/3 | 0/3 | 0 |
| #7 | 0/5 | 2/7 | 2/7 | 29.0 |
| #9 | 0/5 | 1/8 | 1/8 | 13.0 |
| #10 | 1/16 | 4/14 | 4/14 | 29.0 |
| #12 | 0/4 | 0/4 | 0/4 | 0 |
| #13 | 3/11 | 3/8 | 3/8 | 38.0 |
| #14 | 0/7 | 0/7 | 0/7 | 0 |
| #15 | 0/4 | 11/15 | 11/15 | 73.0 |
| #16 | 0/5 | 0/9 | 0/9 | 0 |
| #19 | nt | 0/4 | 0/4 | 0 |
| #20 | 2/12 | 2/12 | 2/12 | 17.0 |
| #21 | 0/11 | 3/14 | 3/14 | 14.0 |
| #22 | 0/1 | 0/4 | 0/4 | 0 |
| #B-6 | nt | 0/8 | 0/8 | 0 |
| #B-17 | nt | 6/13 | 6/13 | 46.0 |
| #B-20 | 0/7 | 0/6 | 0/6 | 0 |
| #B-24 | nt | 0/3 | 0/3 | 0 |
| #B-42 | 0/4 | 0/4 | 0/4 | 0 |
| Control | 23/26 | 23/26 | 23/26 | 88.0 |

[1]FLcpST + GUS (FIG. 2)

TABLE III

ELISA Evaluation of Transgenic MGT-101-14 Heterografted with Infected *C. quinoa*

| Transgenic lines | ELISA Mar. 27, 1997 | ELISA Apr. 31, 1997 | ELISA May 27, 1997 | ELISA Aug. 6, 1997 | (%) infected |
|---|---|---|---|---|---|
| T18,FL(5-1)1[1] | 0/7 | nt | 0/7 | 0/7 | 0 |
| T18,FL(1-1)1[2] | 0/8 | 1/8 | 2/8 | 4/8 | 50.0 |
| T18,FL(1-1)2[2] | 3/4 | 3/4 | 3/4 | 3/4 | 75.0 |
| T18,FL(1-1)3[2] | 2/5 | 3/5 | 4/5 | 4/5 | 80.0 |
| T18,FL(1-1)E[2] | 0/4 | 1/4 | 3/4 | 4/4 | 100.0 |
| T18,FL(B-8)[2] | 0/2 | 1/2 | 2/2 | 2/2 | 100.0 |
| T18,FL(A-3)[2] | nt | 0/4 | 3/4 | 4/4 | 100.0 |
| T18,FL(K-1)[2] | nt | 2/8 | 2/8 | 2/8 | 25.0 |
| CONTROL | — | — | 11/16 | 23/29 | 79 |

[1]FLcpAntiS (FIG. 2); [2]FLcpST (FIG. 2)

TABLE IV

| | | | | |
|---|---|---|---|---|
| Micrografting In vitro | | | | |
| Transgenic L./ GFLV grape | Number of plantlets in GH | ELISA Nov. 27, 1996 | ELISA Jan. 30, 1997 | ELISA Apr. 24, 1997 |
| Riparia #16/ Cabernet sauv. | 5 | 0/2 | 0/2 | 0/2 |
| Riparia #21/ Cabernet sauv. | 5 | 1/5 | 1/5 | 5/5 |
| Riparia #23/ Cabernet sauv. | 5 | 2/5 | 2/5 | 4/5 |
| Riparia #19/ Cabernet sauv. | 4 | 0/4 | 0/4 | 0/4 |
| Riparia B-2/ Cabernet sauv. | 4 | 0/4 | 0/4 | 0/4 |
| Riparia B-13/ Cabernet sauv. | 4 | 1/4 | 2/4 | 3/4 |
| Riparia B-17/ Cabernet sauv. | 2 | 1/2 | 1/2 | 2/2 |
| Riparia B-67/ Cabernet sauv. | 2 | 0/2 | 0/2 | 0/2 |
| Riparia, ht/Cab | 5 | 4/5 | 4/5 | 4/4 |

TABLE V

| | | | | |
|---|---|---|---|---|
| Micrografting In vitro | | | | |
| Transgenic L./ GFLV grape | Number of plantlets in GH | ELISA Nov. 27, 1997 | ELISA Jan. 30, 1997 | ELISA Apr. 24, 1997 |
| Richter 45/Rupestris | 3 | 2/3 | 2/3 | 2/3 |
| Richter 26/Rupestris | 6 | 0/6 | 0/6 | 0/6 |
| Richter 56/Rupestris | 2 | 0/2 | 0/2 | 0/2 |
| Richter 11/Rupestris | 3 | 0/3 | 0/3 | 0/3 |
| Richter 75/Rupestris | 6 | 2/3 | 2/3 | 2/4 |
| Rupestris/Richter 56 | 2 | 0/2 | 0/2 | 0/2 |
| Rupestris/Richter 75 | 6 | 2/3 | 2/3 | 2/5 |
| Rupestris/Richter 4 | 4 | 0/3 | 0/2 | 0/2 |
| Richter ht/Rup | 4 | 3/4 | 3/4 | 4/4 |

Materials and Methods

The above-described results were carried out using the following materials and methods.

Plant Materials

The rootstock cultivars Couderc 3309 ("3309C") (*V. riparia x V. rupestris*), Riparia Gloire ("Gloire") (*V. riparia*), Teleki 5C ("5C") (*V. berlandieri x V. riparia*), MGT 101-14 ("101-14") (*V. riparia x V. rupestris*) and 110 Richter ("110R") (*V. rupestris x V. berlandieri*) were used in the above-described experiments. Callus cultures were initiated from anthers using the methods of Rajasekaram and Mullins (*J. Exp. Bot.* 30: 399–407, 1979). Flower buds of 3309C, 5C, 110R and 101-14 were collected from a vineyard at the Geneva Experiment Station, Geneva, N.Y. Gloire dormant canes were collected from the same vineyard and stored in moist perlite in plastic bags at 4° C. Two to five node sections were rooted in pots with perlite in the greenhouse; floral buds developed within four weeks. Flower buds were harvested prior to anthesis from field-grown vines. Buds were removed from the clusters and surface sterilized in 70% ETOH for one to two minutes. The buds were transferred to 1% sodium hypochlorite for fifteen minutes, then rinsed three times in sterile double-distilled water. Anthers were excised aseptically from flower buds while using a stereo microscope. To determine which state was most favorable for callus induction, the pollen was crushed on a microscope under a coverslip with a drop of acetocarmine to observe the cytological stage according to standard methods.

Media

Four different solid media were used to produce embryos and regenerate plants. The four media used are as follows. (1) Initiation medium. This medium was an amended MS medium (Murashige and Skoog, *Physiol. Plant.* 15: 473–497, 1962) and is referred to as MSE (Mozsar and Sule, *Vitis* 33: 245–246, 1994). (2) Differentiation medium. This medium is referred to as HMG medium as described by Mozsar and Sule (*Vitis* 33: 245–246, 1994); (3) Regeneration medium. This medium is referred to as MGC medium. It is composed of full-strength MS salts amended with 20 g/L sucrose, 4.6 g/L glycerol, 1 g/L casein hydrolysate and 0.8% Noble agar; and (4) Rooting medium. This medium (pH 5.8) is woody plant medium (Lloyd and McCown, *Proc. Intl. Plant Prop. Soc.* 30: 421–427, 1981) supplemented with 0.1 mg/L BA, 3 g/L activated charcoal and 1.5% sucrose.

Somatic Embryogenesis and Regeneration

Anthers were isolated under sterile conditions and plated at a density of forty to fifty anthers per 9.0 cm diameter Petri dish and cultured at 28° C. in the dark. Callus was induced on MSE. After sixty days, embryos were induced and then transferred to hormone-free HMG medium for differentiation. Torpedo-stage embryos were transferred from HMG to MGC medium to promote embryo germination. Cultures were maintained in the dark at 26–28° C. and transferred to fresh medium at three to four week intervals. Hypocotyls (elongated embryos) were transferred to rooting medium in baby food jars (five to eight embryos per jar). The embryos were grown at 25° C. with a daily sixteen hour photoperiod to induce shoot and root formation. After root development plants were transplanted to soil and placed in the greenhouse.

Maintenance and Propagation of Somatic Embryos

Hypocotyls from elongated embryos that developed in HMG or MGC medium were cut into 3–4 mm pieces and placed onto MSE medium to promote the development of secondary embryogenic calli. The secondary embryogenic calli were then transferred to HMG for differentiation and development of new hypocotyls. These secondary hypocotyls from HMG medium were then transferred to MSE medium to obtain a third cycle of embryogenic calli and hypocotyls. The fourth and fifth cycles of embryogenic calli were obtained in a similar manner. Alternatively, embryogenic calli developing from the anthers were propagated on MSE medium to produce sufficient young embryos for transformation. All embryo cultures were transferred at twenty to thirty day intervals to fresh medium for maintenance.

Genes and Vectors

Three genetic constructs were used to genetically transform grape in this study (FIG. 2). *A. tumefaciens* strain C58Z707 containing either the binary plasmid pGA482GG or pGA482G were used to transform the grape plants with GFLV-cp. The coat protein gene of a GFLV designated as 'Geneva' N.Y. isolate CF57 was cloned and sequenced according to standard methods. The coat protein of grapevine fanleaf nepovirus is produced by posttranslational processing of the polyprotein by virus encoded proteinase. The coat protein gene, which is located on the 3' half of the RNA2 genome, does not contain an ATG initiation codon. Oligonucleotide primers containing the NcoI site were therefore used to introduce the translatable initiation codon into a genetic construct. Two primer sets designed to flank the coat protein gene for PCR amplification were utilized according to standard methods. The primer set (P2: cgtcag TCTAGACCATGGTGAGAGGATTAGCTGGTAGAGGAG (SEQ ID NO: 3) and KSL95-10: ctgta CCATGGTCTTTTAAAGTCAGATACC (SEQ ID NO: 4)) was used to generate a translatable construct. To engineer a sense nontranslatable construct, we introduced an additional nucleotide (T) only three nucleotides downstream of the translational initiation codon (ATG) to make a frameshift mutation, as well as to create a stop codon. This was accomplished using the KSL95-10 (SEQ ID NO: 4) and KSL96-15 (acgtta CCATGGTGTAGAGGATTAGCTGGTAGA; SEQ ID NO: 5) primers. (Lower case letters are nonsense sequences which are utilized for effective restriction digestion. Underlined areas are restriction sites which were used for efficient cloning. Bold letters represent the stop codon which was used to engineer a sense nontranslatable construct.) The resulting amplified PCR products were treated with the restriction enzyme, NcoI, and cloned into the plant expression vector pEPT8. Sense or antisense orientation was determined using standard restriction mapping and PCR analysis making use of the positional 35S promoter-specific primer (KSL96-12: agtgct CTCGAGCAATTGAGACTTTTCAACAA; SEQ ID NO: 6) and transgene primers. The expression cassette containing the transgene and plant transcriptional elements, 35S enhancers, 35S promoter, alfalfa mosaic virus RNA4 5' untranslated sequence and 35S terminator was subsequently cloned into the plant transformation vector pGA482G.

Transformation

Transformation protocols were modified from those described by Scorza and Cordts, (*Plant Cell Rep.* 14: 589–592, 1995; Krastanova et al., *Plant Cell Rep.* 24: 550–554, 1995). Overnight cultures of Agrobacterium strain C58Z707 were grown in LB medium at 28° C. in a shaking incubator. Bacteria were centrifuged for five minutes at 5000 rpm (or 3000 rpm) and resuspended in MS liquid medium ($OD_{600}$=0.4–1.0). Callus with globular or heart-shaped embryos was immersed in the bacterial suspension for fifteen to thrity minutes, blotted dry, and transferred to HMG medium with or without acetosyringone (100 uM). The embryogenic calli were cocultivated with the bacteria for forty-eight hours in the dark at 28° C. Next, the plant material was washed in MS liquid plus cefotaxime (300 mg/ml) and carbenicillin (200 mg/ml) two to three times. The material was then transferred to HMG medium containing either 20 or 40 mg/L kanamycin, 300 mg/L cefotaxime, and 200 mg/L carbenicillin to select transgenic embryos. Alternatively, after forty-eight hours of cocultivation with Agrobacterium, embryogenic calli were transferred onto initiation MSE medium containing 25 mg/L kanamycin plus the same antibiotics listed above. All plant material was incubated continuously in the dark at 28° C. After growth on selection medium for three months, embryos were transferred to HMG or MGC without kanamycin for development of hypocotyls. Embryos were then transferred to rooting medium without antibiotics. Nontransformed calli were grown in the same media with and without kanamycin to verify the efficiency of the kanamycin selection and the ability of the plant to regenerate in the presence of the antibiotic.

Analysis of Transgenic Plants

Transgenic plants were analyzed using standard assays GUS assay (Jefferson, *Plant Mol. Biol. Rep.* 5: 387–405, 1987), ELISA for NPTII detection (Cabanes-Bastos et al., *Gene* 77: 69–176, 1989), ELISA for cp detection (Clark et al., *J. Gen. Virol.* 34: 475–483), and PCR and Southern analysis (Ausubel et al., infra).

Isolation of Other Grape Nepovirus-CP Genes

Any grape nepovirus (for example, GFLV) isolate can serve as the nucleic acid source for the molecular cloning of a grape nepovirus coat protein (CP) gene. For example, isolation of a GFLV-CP gene involves the isolation of those DNA sequences which encode a protein exhibiting CP-associated structures, properties, or activities. Based on the GFLV-CP nucleotide and amino acid sequences described herein (FIGS. 1A–1C; SEQ ID NOS: 1 and 2), the isolation of additional GFLV-CP coding sequences is made possible using standard strategies and techniques that are well known in the art.

In one particular example, the GFLV-CP sequences described herein may be used, together with conventional screening methods of nucleic acid hybridization screening. Such hybridization techniques and screening procedures are well known to those skilled in the art and are described, for example, in Benton and Davis, *Science* 196: 180, 1977; Grunstein and Hogness, *Proc. Natl. Acad. Sci., USA* 72: 3961, 1975; Ausubel et al. (supra); Berger and Kimmel (supra); and Sambrook et al., *Molecular Cloning: A Laboratory Manual*, Cold Spring Harbor Laboratory Press, New York. In one particular example, all or part of the 'Geneva' isolate nucleotide sequence (described herein) may be used as a probe to screen a recombinant GFLV DNA library for genes having sequence identity to the coat protein gene of the 'Geneva' isolate. Hybridizing sequences are detected by plaque or colony hybridization according to standard methods, for example those described below.

Alternatively, using all or a portion of the amino acid sequence of the coat protein gene of the 'Geneva' isolate one may readily design GFLV-CP-specific oligonucleotide probes, including GFLV-CP degenerate oligonucleotide probes (i.e., a mixture of all possible coding sequences for a given amino acid sequence). These oligonucleotides may be based upon the sequence of either DNA strand and any appropriate portion of the GFLV-CP sequence (FIGS. 1A–1C; SEQ ID NOS: 1 and 2). General methods for designing and preparing such probes are provided, for example, in Ausubel et al., 1996, *Current Protocols in Molecular Biology*, Wiley Interscience, New York, and Berger and Kimmel, *Guide to Molecular Cloning Techniques*, 1987, Academic Press, New York. These oligonucleotides are useful for GFLV-CP gene isolation, either through their use as probes capable of hybridizing to GFLV-CP complementary sequences or as primers for various amplification techniques, for example, polymerase chain reaction (PCR) cloning strategies. If desired, a combination of different oligonucleotide probes may be used for the screening of a recombinant DNA library. The oligonucleotides may be detectably-labeled using methods known in the art and used to probe filter replicates from a recombinant DNA library. Recombinant DNA libraries are prepared according to methods well known in the art, for example, as described in Ausubel et al. (supra), or they may be obtained from commercial sources.

Other sources of GFLV-CP sequences include those described in Brandt et al., *Arch. Virol.* 140: 157–164, 1995; Margis et al., *J. Gen. Virol.* 74: 1919–1926, 1993; Fuchs et al., *J. Gen Virol.* 955–962, 1989; Serghini et al., *J. Gen. Virol.* 71: 1433–1441, 1990; Bardonnet et al., *Plant Cell Rep.* 13: 357–360, 1994; Krastanova et al., *Plant Cell Rep.* 14: 550–554, 1995; Ritzenthaler et al., *J. Gen. Virol.* 72: 2357–2365, 1991; Mauro et al., *Plant Science*: 112: 97–106, 1995; and Sanchez et al., *Nucleic. Acids. Res.* 19: 5440, 1992. Once GFLV-CP sequence is identified, it is cloned according to standard methods and used for the construction of plant expression vectors as described herein.

Construction of Plant Transigenes

Most preferably, a grape nepovirus coat protein (for example, a GFLV-CP) is expressed as a sense translatable or sense nontranslatable mRNA transcript or as an antisense mRNA transcript by a stably-transfected grape cell line or by a transgenic grapevine or grapevine component. A number of vectors suitable for either stable or extrachromosomal transfection of plant cells, or for the establishment of transgenic plants are available to the public; such vectors are described in Weissbach and Weissbach (*Methods for Plant Molecular Biology*, Academic Press, 1989) and Gelvin et al. (*Plant Molecular Biology Manual*, Kluwer, Academic Publishers, 1990). Methods for constructing such cell lines are described in, for example, Weissbach-and Weissbach (supra), and Gelvin et al. (supra). Example of vectors useful for the expression of transgenes in grapevines are also described in Scorza et al. (*Plant Cell Rep*. 14: 589–592, 1995), Baribault et al. (*J. Expt. Bot*. 41: 1045–1049, 1990), Mullins et al. (*BioTechnology* 8: 1041–1045, 1990), Nakano et al. (*J. Expt. Bot*. 45: 649–656, 1994), Kikkert et al. (*Plant Cell Rep*. 15: 311–316, 1995), Krastanova et al. (*Plant Cell Rep*. 1: 550–554, 1995), Scorza et al. (*Plant Cell Rep*. 14: 589–592, 1994), Scorza et al. (*J. Amer. Soc. Hort. Sci*. 121: 616–619, 1996), Martinelli et al. (*Theor Appl Genet*. 88: 621–628, 1994), and Legall et al. (*Plant Sci*. 102. 161–170, 1994).

Typically, plant expression vectors include (1) a cloned gene (for example, a nucleic acid molecule which expresses a sense translatable, sense nontranslatable, or antisense grape nepovirus RNA) under the transcriptional control of 5' and 3' expression control sequences and (2) a dominant selectable marker. Such plant expression vectors may also contain, if desired, a promoter regulatory region (for example, one conferring inducible or constitutive, pathogen- or wound-induced, environmentally- or developmentally-regulated, or cell- or tissue-specific expression), a transcription initiation start site, a ribosome binding site, an RNA processing signal, a transcription termination site, and/or a polyadenylation signal.

Once the desired grape nepovirus coat protein nucleic acid molecule is obtained as described above, it may be manipulated in a variety of ways known in the art. For example, a GFLV-CP DNA sequence of the invention may, if desired, be combined with other DNA sequences in a variety of ways. The GFLV-CP DNA sequence may be employed with all or part of the gene sequences normally associated with the GFLV-CP. In its component parts, a DNA sequence encoding a GFLV-CP is combined in a DNA construct having a transcription initiation control region capable of promoting transcription in a host-grapevine cell.

In general, the constructs will involve regulatory regions functional in plants which provide for modified production of a GFLV-CP as discussed herein. For example, the sense nontranslatable sequence for a GFLV-CP or fragment thereof will be joined at its 5' end to a transcription initiation regulatory region, for example, such as a sequence naturally found in the 5' upstream region of a plant structural gene. Numerous transcription initiation regions are available which provide for constitutive or inducible regulation.

For applications where developmental, cell, tissue, hormonal, or environmental expression is desired, appropriate 5' upstream non-coding regions are obtained from other genes, for example, from genes regulated during meristem development, seed development, embryo development, leaf development, stem development, or tendril development.

Regulatory transcript termination regions may also be provided in DNA constructs of this invention as well. Transcript termination regions may be provided by the DNA sequence encoding the GFLV-CP or any convenient transcription termination region derived from a different gene source (for example, the NOS or 35S CaMV terminators). The transcript termination region will contain preferably at least 1–3 kb of sequence 3' to the structural gene from which the termination region is derived. Plant expression constructs having GFLV-CP as the DNA sequence of interest for expression (in either the antisense orientation or sense translatable or sense nontranslatable production of mRNA) may be employed with a wide variety of grapevines. Such genetically-engineered plants are useful for a variety of industrial and agricultural applications. Importantly, this invention is applicable to all grapevines or grapevine components, and will be readily applicable to any new or improved transformation or regeneration methods of grape.

The expression constructs include at least one promoter operably linked to at least one sense translatable or sense nontranslatable or antisense GFLV-CP sequence. An example of a useful plant promoter according to the invention is a caulimovirus promoter, for example, a cauliflower mosaic virus (CaMV) promoter. These promoters confer high levels of expression in most plant tissues, and the activity of these promoters is not dependent on virally encoded proteins. CaMV is a source for both the 35S and 19S promoters. In most tissues of transgenic plants, the CaMV 35S promoter is a strong promoter (see, for example, Odell et al., *Nature* 313: 810, 1985). The CaMV promoter is also highly active in monocots (see, for example, Dekeyser et al., *Plant Cell* 2: 591, 1990; Terada and Shimamoto, *Mol. Gen. Genet*. 220: 389, 1990). Moreover, activity of this promoter can be further increased (i.e., between 2–10 fold) by duplication of the CaMV 35S promoter (see for example, Kay et al., *Science* 236: 1299, 1987; Ow et al., *Proc. Natl. Acad. Sci., U.S.A*. 84: 4870, 1987; and Fang et al., *Plant Cell* 1: 141, 1989, and McPherson and Kay, U.S. Pat. No. 5,378,142).

Other useful plant promoters include, without limitation, the nopaline synthase (NOS) promoter (An et al., *Plant Physiol*. 88: 547, 1988), the octopine synthase promoter (Fromm et al., *Plant Cell* 1: 977, 1989), the rice actin promoter (Wu and McElroy, WO91/09948), the cyclase promoter (Chappell et al., WO96/36697), and the cassava vein mosaic virus promoter (Verdaguer et al., *Plant Mol. Biol*. 31: 1129–1139, 1996). Still other exemplary promoters useful in the invention include, without limitation, commelina yellow mottle virus promoter, sugar cane badna virus promoter, rice tungro bacilliform virus promoter, maize streak virus element, and wheat dwarf virus promoter.

For certain applications, it may be desirable to produce the GFLV-CP sequence in an appropriate tissue, at an appropriate level, or at an appropriate developmental time. For this purpose, there are an assortment of gene promoters, each with its own distinct characteristics embodied in its regulatory sequences, shown to be regulated in response to inducible signals such as the environment, hormones, and/or developmental cues. These include, without limitation, gene promoters that are responsible for heat-regulated gene expression (see, for example, Callis et al., *Plant Physiol*. 88: 965, 1988; Takahashi and Komeda, *Mol. Gen. Genet*. 219: 365, 1989; and Takahashi et al. *Plant J*. 2: 751, 1992), light-regulated gene expression (for example, the pea rbcS-3A described by Kuhlemeier et al., *Plant Cell* 1: 471, 1989; the maize rbcS promoter described by Schäffner and Sheen, *Plant Cell* 3: 997, 1991; the chlorophyll a/b-binding protein gene found in pea described by Simpson et al., *EMBO J*. 4: 2723, 1985; the Arabssu promoter; or the rice rbs promoter), hormone-regulated gene expression (for example, the abscisic acid (ABA) responsive sequences from the Em gene of wheat described by Marcotte et al., *Plant Cell* 1: 969, 1989; the ABA-inducible HVA1 and HVA22, and rd29A promoters described for barley and Arabidopsis by Straub et al., *Plant Cell* 6: 617, 1994 and Shen et al., *Plant Cell* 7: 295, 1995; and wound-induced gene expression (for example, of wunI described by Siebertz et al., *Plant Cell* 1: 961, 1989), organ-specific gene expression (for example, of the tuber-specific storage protein gene described by Roshal et al., *EMBO J.* 6: 1155, 1987; the 23-kDa zein gene from maize described by Schernthaner et al., *EMBO J.* 7: 1249, 1988; or the French bean β-phaseolin gene described by Bustos et al., *Plant Cell* 1: 839, 1989), or pathogen-inducible promoters (for example, PR-1, prp-1, or β-1,3 glucanase promoters, the fungal-inducible wirla promoter of wheat, and the nematode-inducible promoters, TobRB7-5A and Hmg-1, of tobacco and parsley, respectively).

Plant expression vectors may also optionally include RNA processing signals, e.g, introns, which have been shown to be important for efficient RNA synthesis and accumulation (Callis et al., *Genes and Dev.* 1: 1183, 1987). The location of the RNA splice sequences can dramatically influence the level of transgene expression in plants. In view of this fact, an intron may be positioned upstream or downstream of a GFLV-CP sequence in the transgene to modulate levels of gene expression.

In addition to the aforementioned 5' regulatory control sequences, the expression vectors may also include regulatory control regions which are generally present in the 3' regions of plant genes (Thornburg et al., *Proc. Natl. Acad. Sci. U.S.A.* 84: 744, 1987; An et al., *Plant Cell* 1: 115, 1989). For example, the 3' terminator region may be included in the expression vector to increase stability of the mRNA. One such terminator region may be derived from the PI-II terminator region of potato. In addition, other commonly used terminators are derived from the octopine or nopaline synthase signals.

The plant expression vector also typically contains a dominant selectable marker gene used to identify those cells that have become transformed. Useful selectable genes for plant systems include genes encoding antibiotic resistance genes, for example, those encoding resistance to hygromycin, kanamycin, bleomycin, G418, streptomycin, or spectinomycin. Genes required for photosynthesis may also be used as selectable markers in photosynthetic-deficient strains. Finally, genes encoding herbicide resistance may be used as selectable markers; useful herbicide resistance genes include the bar gene encoding the enzyme phosphinothricin acetyltransferase and conferring resistance to the broad spectrum herbicide BASTA® (Hoechst AG, Frankfurt, Germany).

In addition, if desired, the plant expression construct may contain a modified or fully-synthetic GFLV-CP sequence which has been changed to enhance the performance of the gene in plants.

It should be readily apparent to one skilled in the art of molecular biology, especially in the field of plant molecular biology, that the level of gene expression is dependent, not only on the combination of promoters, RNA processing signals, and terminator elements, but also on how these elements are used to increase the levels of selectable marker gene expression.

Grapevine Transformation

Upon construction of the plant expression vector, several standard methods are available for introduction of the vector into a plant host, thereby generating a transgenic plant. These methods include (1) Agrobacterium-mediated transformation (*A. tumefaciens* or *A. rhizogenes*) (see, for example, Lichtenstein and Fuller In: *Genetic Engineering*, vol 6, PWJ Rigby, ed, London, Academic Press, 1987; and Lichtenstein. C. P., and Draper, J,. In: *DNA Cloning*, Vol II, D. M. Glover, ed, Oxford, IRI Press, 1985)), (2) the particle delivery system (see, for example, Gordon-Kamm et al., *Plant Cell* 2: 603 (1990); or Sanford et al. U.S. Pat. Nos. 4,945,050, 5,036,006, and 5,100,792,), (3) microinjection protocols (see, for example, Green et al., supra), (4) polyethylene glycol (PEG) procedures (see, for example, Draper et al., *Plant Cell Physiol.* 23: 451, 1982; or for example, Zhang and Wu, *Theor. Appl. Genet.* 76: 835, 1988), (5) liposome-mediated DNA uptake (see, for example, Freeman et al., *Plant Cell Physiol.* 25: 1353, 1984), (6) electroporation protocols (see, for example, Gelvin et al., supra; Dekeyser et al., supra; Fromm et al., *Nature* 319: 791, 1986; Sheen *Plant Cell* 2: 1027, 1990; or Jang and Sheen *Plant Cell* 6: 1665, 1994), and (7) the vortexing method (see, for example, Kindle supra). The method of transformation is not critical to the invention. Any method which provides for efficient transformation may be employed. Some exemplary methods for transforming grapes are found in Scorza et al. (*Plant Cell Reports* 14: 589–592, 1995), Baribault et al. (*J. Expt. Bot.* 41: 1045–1049, 1990), Mullins et al. (*BioTechnology* 8: 1041–1045, 1990), Nakano et al. (*J. Expt. Bot.* 45: 649–656, 1994), Kikkert et al. (*Plant Cell Rep.* 15: 311–316, 1995), Krastanova et al. (*Plant Cell Rep.* 1: 550–554, 1995), Scorza et al. (*Plant Cell Rep.* 14: 589–592, 1994), Scorza et al. (*J. Amer. Soc. Hort. Sci.* 121: 616–619, 1996), Martinelli et al. (*Theor Appl Genet.* 88: 621–628, 1994), and Legall et al. (*Plant Sci.* 102. 161–170, 1994). As newer methods are available to transform crops or other host cells, they may be directly applied as well.

Suitable plants for use in the practice of the invention include, but are not limited to, grapevines (for example, Vitis spp., Vitis spp. hybrids, and all members of the subgenera Euvitis and Muscadinia), including scion or rootstock cultivars. Exemplary scion cultivars include, without limitation, those which are referred to as table or raisin grapes and those used in wine production such as Cabernet Franc, Cabernet Sauvignon, Chardonnay (for example, CH 01, CH 02, CH Dijon), Merlot, Pinot Noir (PN, PN Dijon), Semillon, White Riesling, Lambrusco, Thompson Seedless, Autumn Seedless, Niagrara Seedless, and Seval Blanc. Other scion cultivars which can be used include those commonly referred to as Table or Raisin Grapes, such as Alden, Almeria, Anab-E-Shahi, Autumn Black, Beauty Seedless, Black Corinth, Black Damascus, Black Malvoisie, Black Prince, Blackrose, Bronx Seedless, Burgrave, Calmeria, Campbell Early, Canner, Cardinal, Catawba, Christmas, Concord, Dattier, Delight, Diamond, Dizmar, Duchess, Early Muscat, Emerald Seedless, Emperor, Exotic, Ferdinand de Lesseps, Fiesta, Flame seedless, Flame Tokay, Gasconade, Gold, Himrod, Hunisa, Hussiene, Isabella, Italia, July Muscat, Khandahar, Katta, Kourgane, Kishmishi, Loose Perlette, Malaga, Monukka, Muscat of Alexandria, Muscat Flame, Muscat Hamburg, New York Muscat, Niabell, Niagara, Olivette blanche, Ontario, Pierce, Queen, Red Malaga, Ribier, Rish Baba, Romulus, Ruby Seedless, Schuyler, Seneca, Suavis (IP 365), Thompson seedless, and Thomuscat. They also include those used in wine production, such as Aleatico, Alicante Bouschet, Aligote, Alvarelhao, Aramon, Baco blanc (22A), Burger, Cabernet franc, Cabernet, Sauvignon, Calzin, Carignane, Charbono; Chardonnay, Chasselas dore, Chenin blanc, Clairette blanche, Early Burgundy, Emerald Riesling, Feher Szagos, Fernao Pires, Flora, French Colombard, Fresia, Furmint, Gamay, Gewurztraminer, Grand noir, Gray Riesling, Green Hungarian, Green Veltliner, Grenache, Grillo, Helena, Inzolia, Lagrein, Lambrusco de Salamino, Malbec, Malvasia bianca, Mataro, Melon, Merlot, Meunier, Mission, Montua de Pilas, Muscadelle du Bordelais, Muscat blanc, Muscat Ottonel, Muscat Saint-Vallier, Nebbiolo, Nebbiolo fino, Nebbiolo Lampia, Orange Muscat, Palomino, Pedro Ximenes, Petit Bouschet, Petite Sirah, Peverella, Pinot noir, Pinot Saint-George, Primitivo di Gioa, Red Veltliner, Refosco, Rkatsiteli, Royalty, Rubired, Ruby Cabernet, Saint-Emilion, Saint Macaire, Salvador, Sangiovese, Sauvignon blanc, Sauvignon gris, Sauvignon vert, Scarlet, Seibel 5279, Seibel 9110, Seibel 13053, Semillon, Servant, Shiraz, Souzao, Sultana Crimson, Sylvaner, Tannat, Teroldico, Tinta Madeira, Tinto cao, Touriga, Traminer, Trebbiano Toscano, Trousseau, Valdepenas, Viognier, Walschriesling, White Riesling, and Zinfandel.

Rootstock cultivars that are useful in the invention include, without limitation, *Vitis rupestris* Constantia, *Vitis rupestris* St. George, *Vitis california, Vitis girdiana, Vitis rotundifolia, Vitis rotundifolia* Carlos, Richter 110 (*Vitis berlandieri x rupestris*), 101-14 Millarder et de Grasset (*Vitis riparia x rupestris*), Teleki 5C (*Vitis berlandieri x riparia*), 3309 Courderc (*Vitis riparia x rupestris*), Riparia Gloire de Montpellier (*Vitis riparia*), 5BB Teleki (selection Kober, *Vitis berlandieri x riparia*), $SO_4$ (*Vitis berlandieri x rupestris*), 41B Millardet (*Vitis vinifera x berlandieri*), and 039-16 (*Vitis vinifera x Muscadinia*). Additional rootstock cultivars which can be used include Couderc 1202, Couderc 1613, Couderc 1616, Couderc 3309, Dog Ridge, Foex 33EM, Freedom, Ganzin 1 (A×R #1), Harmony, Kober 5BB, LN33, Millardet & de Grasset 41B, Millardet & de Grasset 420A, Millardet & de Grasset 101-14, Oppenheim 4 (SO4), Paulsen 775, Paulsen 1045, Paulsen 1103, Richter 99, Richter 110, Riparia Gloire, Ruggeri 225, Saint-George, Salt Creek, Teleki 5A, Vitis rupestris Constantia, *Vitis california*, and *Vitis girdiana.*

In general, transfer and expression of transgenes in plant cells, including grape plants, are now routine practices to those skilled in the art, and have become major tools to carry out gene expression studies in plants and to produce improved plant varieties of agricultural or commercial interest.

Transgenic Grapevine Regeneration

Plant cells transformed with a plant expression vector can be regenerated, for example, from single cells, callus tissue, or leaf discs according to standard plant tissue culture techniques. It is well known in the art that various cells, tissues, and organs from almost any plant can be successfully cultured to regenerate an entire plant; such techniques are described, for example, in Vasil supra; Green et al., supra; Weissbach and Weissbach, supra; and Gelvin et al., supra.

In one particular example, a cloned sense nontranslatable GFLV-CP sequence (for example, a sense translatable or sense nontranslatable coat protein gene, or an antisense construct) construct (for example, a GFLV-CP sequence in the sense orientation having an out-of-reading frame ATG including a stop codon after the initiation codon) under the control of the 35S CaMV promoter and the nopaline synthase terminator and carrying a selectable marker (for example, kanamycin resistance) is transformed into Agrobacterium. Transformation of grapevine with vector-containing Agrobacterium is carried out as described by Scorza and Cordts. Putative transformants are selected after a few weeks on plant tissue culture media containing kanamycin. Kanamycin-resistant plant material is then placed on plant tissue culture media without hormones for root initiation.

Transgenic plants expressing the selectable marker are then screened for transmission of the transgene DNA by standard detection techniques as described above. Each positive transgenic plant and its transgenic progeny are unique in comparison to other transgenic plants established with the same transgene. Integration of the transgene DNA into the plant genomic DNA is in most cases random, and the site of integration can profoundly affect the levels and the tissue and developmental patterns of transgene expression. Consequently, a number of transgenic lines are usually screened for each transgene to identify and select plants with the most appropriate expression profiles.

Transgenic lines are evaluated for levels of transgene expression. Expression at the RNA level is determined initially to identify and quantitate expression-positive plants. Standard techniques for RNA analysis are employed and include Northern blot assays and nuclear run-off assays (see, for example, Ausubel et al., supra). The RNA-positive plants are then analyzed for resistance to GFLV infection using the methods described above. Transformed grapevines that express a sense nontranslatable GFLV-CP sequence having resistance to fanleaf disease relative to control plants are taken as being useful in the invention.

All publications and patent applications mentioned in this specification are herein incorporated by reference to the same extent as if each independent publication or patent application was specifically and individually indicated to be incorporated by reference.

What is claimed is:

1. An isolated nucleic acid molecule encoding a protein comprising an amino acid sequence having at least 99% amino acid identity to the amino acid sequence of the 'Geneva' isolate grapevine fanleaf virus coat protein of SEQ ID NO: 2, and wherein said nucleic acid molecule, when expressed in grapevine, confers increased resistance against grapevine fanleaf virus.

2. The isolated nucleic acid molecule of claim 1, wherein said protein comprises the amino acid sequence of SEQ ID NO: 2.

3. The isolated nucleic acid molecule of claim 1, wherein said protein consists of the amino acid sequence of SEQ ID NO: 2.

4. The isolated nucleic acid molecule of claim 1, wherein said nucleic acid molecule is operably linked to an expression control region.

5. A vector comprising an isolated nucleic acid molecule encoding a protein comprising an amino acid sequence having at least 99% amino acid identity to the amino acid sequence of the 'Geneva' isolate grapevine fanleaf virus coat protein of SEQ ID NO: 2, and wherein said nucleic acid molecule, when expressed in grapevine, confers increased resistance against grapevine fanleaf virus.

6. The vector of claim 5, wherein said nucleic acid molecule is positioned for expression of a sense translatable RNA transcript.

7. The vector of claim 5, wherein said nucleic acid molecule is positioned for expression of a sense nontranslatable RNA transcript.

8. The vector of claim 5, wherein said nucleic acid molecule is positioned for expression of an antisense RNA sequence.

9. A plant cell transformed with the vector of claim 5.

10. A transgenic plant or plant component comprising the vector of claim 5.

11. The transgenic plant or plant component of claim 10, wherein said nucleic acid molecule is expressed in said plant as a sense translatable RNA transcript.

12. The transgenic plant or plant component of claim 10, wherein said nucleic acid molecule is expressed in said plant as a sense nontranslatable RNA transcript.

13. The transgenic plant or plant component of claim 10, wherein said nucleic acid molecule is expressed in said plant as an antisense RNA transcript.

* * * * *